United States Patent
Afonin et al.

(10) Patent No.: US 9,481,712 B2
(45) Date of Patent: Nov. 1, 2016

(54) PEPTIDOMIMETICS POSSESSING PHOTO-CONTROLLED BIOLOGICAL ACTIVITY

(71) Applicants: KARLSRUHER INSTITUT FÜR TECHNOLOGIE, Karlsruhe (DE); NATIONAL TARAS SHEVCHENKO UNIVERSITY OF KYIV, Kyiv (UA)

(72) Inventors: Sergiy Afonin, Karlsruhe (DE); Oleg Babii, Karlsruhe (DE); Igor Komarov, Pukhivka (UA); Pavlo Mykhailiuk, Kyiv (UA); Anne Ulrich, Karlsruhe (DE)

(73) Assignees: Karlsruher Institut Für Technologie, Karlsruhe (DE); National Taras Shevchenko University, Kyiv (UA)

( * ) Notice: Subject to any disclaimer, the term of this patent is extended or adjusted under 35 U.S.C. 154(b) by 0 days.

(21) Appl. No.: 14/769,275

(22) PCT Filed: Feb. 24, 2014

(86) PCT No.: PCT/EP2014/000482
§ 371 (c)(1),
(2) Date: Aug. 20, 2015

(87) PCT Pub. No.: WO2014/127919
PCT Pub. Date: Aug. 28, 2014

(65) Prior Publication Data
US 2015/0376236 A1 Dec. 31, 2015

(30) Foreign Application Priority Data
Feb. 22, 2013 (EP) ..................................... 13000893

(51) Int. Cl.
*A61K 38/00* (2006.01)
*C07K 5/00* (2006.01)
*C07K 7/00* (2006.01)
*C07K 16/00* (2006.01)
*C07K 17/00* (2006.01)
*C07K 7/66* (2006.01)
*C07K 7/06* (2006.01)
*C07D 333/38* (2006.01)

(52) U.S. Cl.
CPC ............... *C07K 7/66* (2013.01); *C07D 333/38* (2013.01); *C07K 7/06* (2013.01)

(58) Field of Classification Search
CPC ........... A61K 38/00; C07K 2/00; C07K 7/06
See application file for complete search history.

(56) References Cited

FOREIGN PATENT DOCUMENTS

WO 0220769 A1 3/2002

OTHER PUBLICATIONS

Fujimoto, et al., Photoswitchable, DNA-Binding Helical Peptides Assembled with Two Independently Designed Sequences for Photoregulation and DNA Recognition, Chem. Eur. J. 2012, vol. 18, pp. 9834-9840.
Blanco-Lomas, et al., Reversible Photocontrol of Peptide Conformation with a Rhodopsin-like Photoswitch, J. Am. Chem. Soc., 2012, vol. 134, pp. 6960-6963.
Wachtveitl, et al., Ultrafast Conformational Dynamics in Cyclic Azobenzene Peptides of Increased Flexibility, Biophysical Journal, 2004, vol. 86, pp. 2350-2362.
Schütt, et al., Photocontrol of Cell Adhesion Breif Communication Processes: Model Studies with Cyclic Azobenzene-RGD Peptides, Chemistry & Biology, vol. 10, pp. 487-490, Jun. 2003.

*Primary Examiner* — Hasan Ahmed
*Assistant Examiner* — Kaipeen Yang
(74) *Attorney, Agent, or Firm* — Stinson Leonard Street LLP

(57) ABSTRACT

The present invention relates to pharmaceutically and/or diagnostically active compounds, in particular peptide analogs (peptidomimetics), which can be reversibly controlled between an active and an inactive state by irradiation with light of different wavelengths. The present invention further relates to an intermediate compound usable in the manufacture of such pharmaceutically and/or diagnostically active compounds, as well as a manufacturing method thereof.

5 Claims, 10 Drawing Sheets

SEQUENCE LISTING

<160> NUMBER OF SEQ ID NOS: 4

<210> SEQ ID NO 1
<211> LENGTH: 10
<212> TYPE: PRT
<213> ORGANISM: Brevibacillus brevis
<220> FEATURE:
<221> NAME/KEY: MISC_FEATURE
<222> LOCATION: (1)..(10)
<223> OTHER INFORMATION: cyclic
<220> FEATURE:
<221> NAME/KEY: MOD_RES
<222> LOCATION: (3)..(3)
<223> OTHER INFORMATION: Orn
<220> FEATURE:
<221> NAME/KEY: MISC_FEATURE
<222> LOCATION: (5)..(5)
<223> OTHER INFORMATION: D-phenylalanine
<220> FEATURE:
<221> NAME/KEY: MOD_RES
<222> LOCATION: (8)..(8)
<223> OTHER INFORMATION: Orn
<220> FEATURE:
<221> NAME/KEY: MISC_FEATURE
<222> LOCATION: (10)..(10)
<223> OTHER INFORMATION: D-phenylalanine

<400> SEQUENCE: 1

Pro Val Xaa Leu Xaa Pro Val Xaa Leu Xaa
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(8)
<223> OTHER INFORMATION: part of cyclic peptidomimetic
<220> FEATURE:
<221> NAME/KEY: MOD_RES
<222> LOCATION: (3)..(3)
<223> OTHER INFORMATION: Orn -continued

```
<220> FEATURE:
<221> NAME/KEY: MISC_FEATURE
<222> LOCATION: (5)..(5)
<223> OTHER INFORMATION: D-phenylalanine
<220> FEATURE:
<221> NAME/KEY: MOD_RES
<222> LOCATION: (8)..(8)
<223> OTHER INFORMATION: Orn

<400> SEQUENCE: 2

Pro Val Xaa Leu Xaa Pro Val Xaa
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(8)
<223> OTHER INFORMATION: part of a cyclic peptidomimetic
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (4)..(4)
<223> OTHER INFORMATION: D-phenylalanine
<220> FEATURE:
<221> NAME/KEY: MOD_RES
<222> LOCATION: (7)..(7)
<223> OTHER INFORMATION: Orn

<400> SEQUENCE: 3

Val Xaa Leu Xaa Pro Val Xaa Leu
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Orn
<220> FEATURE:
<221> NAME/KEY: MISC_FEATURE
<222> LOCATION: (1)..(8)
<223> OTHER INFORMATION: part of a cyclic peptidomimetic
<220> FEATURE:
<221> NAME/KEY: MISC_FEATURE
<222> LOCATION: (3)..(3)
<223> OTHER INFORMATION: D-phenylalanine
<220> FEATURE:
<221> NAME/KEY: MOD_RES
<222> LOCATION: (6)..(6)
<223> OTHER INFORMATION: Orn
<220> FEATURE:
<221> NAME/KEY: MISC_FEATURE
<222> LOCATION: (8)..(8)
<223> OTHER INFORMATION: D-phenylalanine

<400> SEQUENCE: 4

Xaa Leu Xaa Pro Val Xaa Leu Xaa
1               5
```

PEPTIDOMIMETICS POSSESSING PHOTO-CONTROLLED BIOLOGICAL ACTIVITY

This application claims priority to International Publication Number WO 2014/127919, filed on Feb. 24, 2014, which claims priority to European Patent Application No. 13000893.1, filed on Feb. 22, 2013, each of which are hereby incorporated by reference herein in their entireties.

A paper copy of the Sequence Listing and a computer readable form of the Sequence Listing containing the file named "K4925US-uh(3004751-0003)_ST25.txt", which is 2,265 bytes in size (as measured in MICROSOFT WINDOWS® EXPLORER), are provided herein and are herein incorporated by reference. This Sequence Listing consists of SEQ ID NO:1-4.

The present invention relates to pharmaceutically and/or diagnostically active compounds, such as peptide analogues (peptidomimetics), which can be reversibly controlled between an active and an inactive state by irradiation with light of different wavelengths. The present invention further relates to an intermediate compound usable in the manufacture of such pharmaceutically and/or diagnostically active compounds, as well as a manufacturing method thereof.

One of the main problems in drug-based therapy and diagnosis is the limited specificity of the pharmaceutically and/or diagnostically active compounds, which may cause undesired side-effects, particularly in regions of healthy tissue or in bodily fluids of a patient. These side-effects result in lower therapeutic indices which limit the effective use of the respective drugs.

Consequently, efforts have been made to identify drugs which specifically act at the desired site of action, such as localized viral, bacterial, fungal or parasitic infection, inflammation, wounds, hemorrhages, or hyperplastic, neoplastic, sclerotic, thrombotic and necrotic disorders. One concept to achieve this goal is to design drugs which predominantly accumulate in the target tissue so that their concentrations—and thus their undesired side-effects—are significantly reduced in healthy tissues or bodily fluids. Another approach to reduce the above-mentioned side-effects and increase the therapeutic index of a drug is the administration of an inactive form of the drug, e.g. as a prodrug, and the conversion of said inactive form at the desired site of action, using for example electromagnetic irradiation.

For instance, peptidomimetics, whose biological activity can be controlled by light of different wavelengths, have been described in the literature [Winner, I.; Rubin, I. Control of the structure and functions of biomaterials by light. *Angew. Chem., Int. Ed. Engl.* 1996, 35, 367-385]. Most of these peptidomimetics contain azobenzene photo-isomerizable fragments (Scheme 1), which can change their conformation from the thermodynamically more stable trans- to the less stable cis-conformation upon exposure to UV light, and from cis to trans upon illumination by exposure to visible light.

Scheme 1: Azobenzene-derived photo-sensitive peptidomimetics in a general representation. The reversibly photo-isomerizable azobenzene molecular fragment (enclosed by the dashed lines) is incorporated into a polypeptide chain (PP).

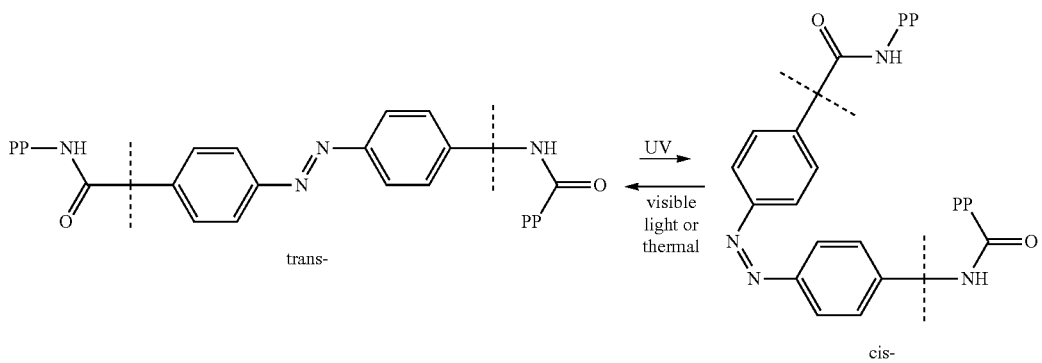

Photo-isomerization of the azobenzene fragments results in a change of the overall structure and biological activity of the corresponding peptidomimetics. A drawback of peptidomimetics bearing the azobenzene moiety is the thermal instability of this photo-sensitive fragment: the cis-configuration of the azobenzene unit converts to the trans-configuration not only upon exposure to visible light, but also spontaneously at ambient temperature (10-30° C.). Other drawbacks of azobenzene-derived peptidomimetics are their low photo-conversion efficiency, low photostability and potential toxicity [H. Mori, Y. Mori, S. Sugie, N. Yoshimi, M. Takahashi, H. Ni-i, H. Yamazaki, K. Toyoshi, G. M. Williams. Genotoxicity of a variety of azobenzene and aminoazobenzene compounds in the hepatocyte/DNA repair test and the *Salmonella*/mutagenicity test. *Cancer Res.* 1986, 46, 1654-1658].

The principle of photo-activating the biological activity has also been used in so-called "caged peptides" [Yasushi Shigeri, Yoshiro Tatsu, Noboru Yumoto. Synthesis and application of caged peptides and proteins. *Pharmacology & Therapeutics* 2001, 91, 85-92]. Caged peptides contain covalently attached groups that are rapidly cleaved upon exposure to light of a specific wavelength. Attachment of photo-labile groups makes the molecule inert, until photolysis converts it into its bioactive derivative. When the caged peptides need to be activated, the concentration jump of biologically active substances can be brought about instantly in a limited area by irradiation with pulsed and focused light of specific wavelength. Photo-activation of the caged peptides is non-reversible. It might bring about not only the desired biological activity (e.g. antimicrobial, antineoplastic, immunostimulating or enzyme-modulating), but also some undesirable effects (e.g. toxic, inflammatory or stress-inducing), which might cause side-effects when the peptides are used as chemotherapeutics, and therefore require elaboration of the strategies to eliminate the compound post-therapeutically.

All of the above-mentioned compounds suffer from a variety of drawbacks such as thermal instability, low conversion efficiency, low photostability, and a potential toxicity. Consequently, there is a constant need of novel compounds which avoid the above-described problems and allow the specific treatment of localized disorders.

Accordingly, the problem underlying the present invention is to provide pharmaceutically and/or diagnostically active compounds, such as peptidomimetics, which allow an effective and reversible conversion between their pharmaceutically and/or diagnostically inactive and active forms, and which are thermally stable in both forms and resistant to photo-destruction and proteases.

This problem is solved according to the present invention by providing, as a first aspect, a peptidomimetic compound represented by the general formula Ia or a salt thereof,

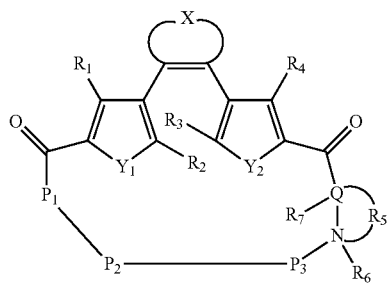

Ia wherein $R_1$ and $R_4$ are independently selected from the group consisting of H, an alkyl group, alkenyl group, alkynyl group, alkoxy group, aryl group, heteroaryl group, cyano group, nitro group, phosphate group, sulfoxyl group or any other optionally substituted group;
$R_2$ and $R_3$ are independently selected from an alkyl group, alkenyl group, alkynyl group, alkoxy group, aryl group, heteroaryl group, cyano group, nitro group, phosphate group, sulfoxyl group or any other optionally substituted group;
X represents —$(CH_xF_y)_z$—, wherein x+y=2, x=0, 1 or 2, y=0, 1 or 2, and z=2 to 4;
$Y_1$ and $Y_2$ are independently selected from S, O and N, or their derivatives like $SO_2$ or N-alkyl;
$P_1$ and $P_3$ each independently represents a single amino acid residue or a peptide sequence of 2 or more amino acid residues;
$P_2$ is absent or represents a single amino acid residue or a peptide sequence of 2 or more amino acid residues;
Q is C or N;
$R_5$ is selected from H, an alkyl group, heteroalkyl group, alkenyl group, heteroalkenyl group, alkynyl group or a heteroalkynyl group, and is bound to Q or may form a ring together with Q and N, or $R_5$ is absent;
$R_6$ is selected from H, an alkyl group, heteroalkyl group, alkenyl group, heteroalkenyl group, alkynyl group, heteroalkynyl group, alkoxy group, aryl group, and heteroaryl group, or is absent; and
$R_7$ is selected from H, an amino acid side chain, an alkyl group, heteroalkyl group, alkenyl group, heteroalkenyl group, alkynyl group, heteroalkynyl group, alkoxy group, aryl group or a heteroaryl group;

with the proviso that when $P_2$ is absent, $P_1$ and $P_3$ are not bonded to each other;
with the proviso that when Q is N, $R_5$ is absent, and
with the proviso that when $R_5$ forms a ring together with Q and N, $R_6$ is absent.

According to the present invention, the peptidomimetic compound of formula Ia further includes all possible stereo- and regioisomers with regard to groups $R_5$, $R_6$, $R_7$, Q and $P_1$ to $P_3$.

In the following, the general group

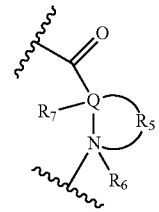

will be also referred to as "linker group".

According to the present invention, $R_5$ is a monovalent group which is bound to Q or is a bivalent group which may form a ring together with Q and N.

As such, the structural element

includes both above cases, wherein $R_5$ is bound to Q as a monovalent group, or bridges Q and N to form a ring containing Q, $R_5$ and N. Therefore, the above structural element may also be expressed as the two individual forms it can represent:

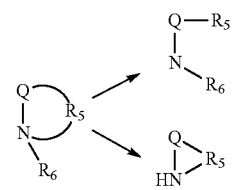

For example, $R_5$ may be H, e.g. in a linker group representing the amino acid valine, or may form a ring together with Q and N, e.g. in a linker group representing the amino acid proline. In the latter case where $R_5$ forms a ring together with Q and N, $R_6$ is absent. Examples are given below as follows:

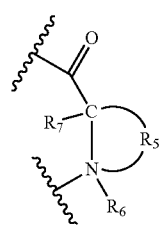 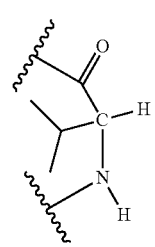

general structure of the
linker group (Q = C)      linker group = valine

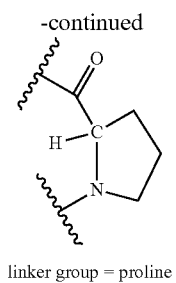

linker group = proline

Herein, the group $R_6$ is bound to N or, when $R_5$ forms a ring together with Q and N, is absent.

According to the present invention, the group $R_7$ is bound to Q and may inter alia represent an amino acid side chain. In this context, the term "amino acid side chain" is not particularly limited and includes side chains of non-natural and natural amino acids. According to a preferred embodiment of the present invention, $R_7$ represents an amino acid side chain of a natural amino acid, such as a hydroxymethyl group (serine) or an isopropyl group (valine).

The present invention further includes all stereoisomers of the group Q, i.e. for example, when $R_7$ represents an amino acid side chain, D- and L-configurations are included within the scope of the present invention.

According to an especially preferred example, $R_1$ and $R_4$ are H. According to another especially preferred example $R_2$ and $R_3$ are methyl. According to another especially preferred example X is —$CH_2CH_2CH_2$— or —$CF_2CF_2CF_2$—. According to another especially preferred example each of $Y_1$ and $Y_2$ is S. According to another especially preferred example, Q is C. According to another especially preferred example, Q is N, $R_6$ and $R_7$ is H, and $R_5$ is absent. According to a further especially preferred embodiment of the present invention, Q is C, $R_5$ is H and $R_7$ is an amino acid side chain.

As a further aspect, the present invention provides a peptidomimetic compound represented by the general formula Ib or a salt thereof,

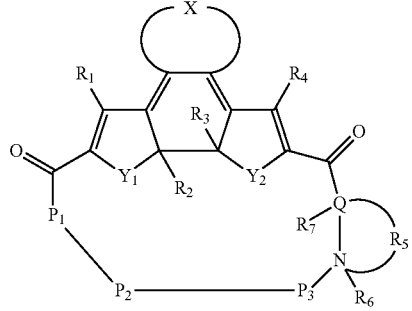

wherein $R_1$ to $R_4$, X, $Y_1$, $Y_2$, $P_1$ to $P_3$, Q, and $R_5$ to $R_7$ are as defined above, with the proviso that when $P_2$ is absent, $P_1$ and $P_3$ are not bonded to each other, with the proviso that when Q is N, $R_5$ is absent, and with the proviso that when $R_5$ forms a ring together with Q and N, $R_6$ is absent.

The above-defined peptidomimetic compound represented by formula Ib further includes, in addition to those mentioned above for formula Ia, all possible stereo- and regioisomers with regard to $R_2$ and $R_3$.

According to the present invention, the above-defined compounds Ia and Ib represent two photo-interconvertible isomeric forms which can be converted into each other by irradiation with light of different wavelengths and exist in an "open" form and a "closed" form (cf. the following Scheme 2). Significantly, the "open" form is more flexible than the conformationally restrained "closed" form.

Scheme 2: the diarylethene photo-switchable molecular system incorporated in a polypeptide backbone chain.

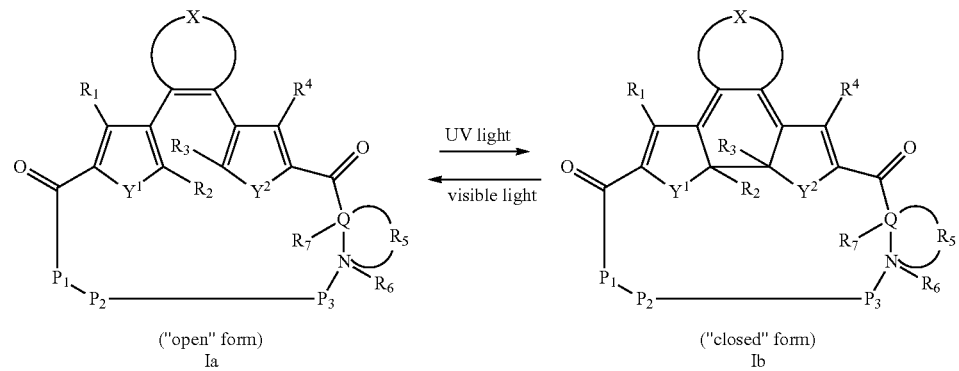

This is achieved by incorporating the diarylethene-derived photo-switchable molecular system shown in the following Scheme 3 into the backbone of a peptidomimetic compound, whereby the activity of said peptidomimetic compounds can be effectively controlled.

Scheme 3: The diarylethene photo-switchable molecular system (enclosed by the dashed lines).

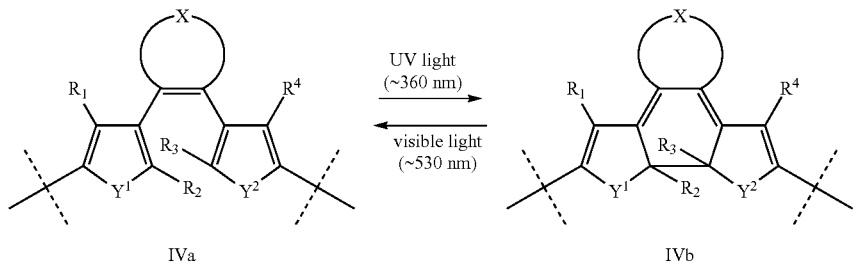

IVa

IVb

Herein, the expressions "photo-switchable molecular system", "photo-switchable fragment", "photo-switchtable building block", "photo-switchable diarylethene fragment" or "photo-switchable diarylethene group" may be used synonymously and relate to the interconvertible diarylethene moiety as shown in the above Scheme 3, which may be present in said open or closed forms.

According to the present invention, photo-isomerization of the diarylethene photo-switchable fragment from the "open" to the "closed" form may be achieved by irradiation with ultraviolet (UV) light. For example, conversion of the open form into the closed from may be carried out by irradiation with light having a wavelengths in the range of 100 to 500 nm, such as 200 to 300 nm, 250 to 380 nm, or 300 to 500 nm, depending on the exact chemical nature of the photo-switch. On the other hand, photo-isomerization of the diarylethene photo-switchable fragment from the closed form to the open form may be achieved by irradiation with longer wavelength light, such as visible (VIS) or infrared, depending on the exact chemical nature of the photo-switch. For example, conversion of the open form into the closed from may generally be carried out by irradiation with light having a wavelength in the range of 300 to 12.000 nm, such as 300 to 400 nm, 350 to 8.000 nm or 500 to 5.000 nm. According to a preferred embodiment of the present invention, conversion of the open form into the closed from may be carried out by irradiation with light having a wavelength in the range of 380 to 740 nm, such as 420 to 680 nm, 480 to 600 nm.

Herein, the term "peptidomimetic" is not specifically restricted and generally includes both cyclic and linear compounds which comprise the diarylethene photo-switchable fragment as a part of the peptidomimetic backbone and one or more natural or non-natural amino acid residues, and which exert a pharmaceutic and/or diagnostic activity in at least their "open" or "closed" form. For example, according to the present invention, peptidomimetic compounds may be based on naturally occurring or designed peptides, which have been altered, e.g. by modifying, deleting and/or incorporating one or more amino acid residues.

As used herein, the expression "pharmaceutically and/or diagnostically active" is not specifically restricted and includes any activity which may be exploited in therapy, prophylaxis or diagnosis of a disorder in a patient, such as antimicrobial, antiviral, antifungal, antiparasitic, antiproliferative, cytostatic, cytotoxic, cytolytic, anticancer, antirheumatic, cardiovascular, reproductive controlling, anti/pro-inflammatory, activatory, inhibitory, agonistic, antagonistic and sensitizing activity, or activity which allows to visualize specific tissues or bodily fluids, e.g. by staining or visualization in imaging applications. Herein, the expressions "pharmaceutically active" and "biologically active" are used synonymously.

According to the present invention, the above-defined peptidomimetic compounds may generally be based on any suitable template peptide, e.g. as in β-hairpins or loops, including linear or cyclic antibiotic peptides, such as Gramicidin S, various tyrocidins, polymyxins (e.g. Polymyxin B), bacitracins, actinomycines, tachyplesins, protegrins, polyphemusins, defensins, antimicrobial glycopeptides (e.g. Vancomycin), lantibiotics (e.g. Nisin), lipopeptide antibiotics (e.g. Daptomycin); and anti-cancer peptides, such as Gomesin, Lactoferricin B and cryptophycins; immunosuppressive cyclosporins; hepatotoxic microcystins; antifungal laxaphycins; antiviral (ionophoric) Valinomycin and other (bacteriostatic) streptogramins; enzyme inhibitors, such as cyclotheonamides, Sunflower trypsin inhibitor, micropeptins, amanitins, microviridins; integrin-antagonistic RGD-peptides; antianaiogenic NGR-peptides; SH2-domain-binding phosphopeptides; peptide hormones (e.g. Somatostatin, Oxytocin, Melanin-concentrating hormone); various cyclopeptides and derivatives thereof, etc.

As used herein, the term "alkyl" generally includes a straight chain or branched chain of carbon atoms, which may optionally be substituted. The alkyl group is preferably a $C_1$-$C_{12}$ alkyl group, a $C_1$-$C_8$ alkyl group, a $C_1$-$C_6$ alkyl group, or a $C_1$-$C_4$ alkyl group. The same definition applies to the terms "alkenyl" and "alkynyl", with the exception that "alkenyl" includes at least one carbon-carbon double bond, wherein "alkynyl" includes at least one carbon-carbon triple bond. According to the present invention, alkyl, alkenyl and alkynyl groups may also be in cyclic form.

Herein, the term "optionally substituted" includes the replacement of hydrogen atoms with other functional groups on the radical that is optionally substituted. Such other functional groups include amino groups, hydroxyl groups, halo groups, thiol groups, alkyl groups, haloalkyl groups, heteroalkyl groups, aryl groups, arylalkyl groups, arylheteroalkyl groups, nitro groups, sulfonic acid groups and derivatives thereof, as well as carboxylic acid groups and derivatives thereof. Moreover, any of said amino groups, hydroxyl groups, thiol groups, alkyl groups, haloalkyl groups, heteroalkyl groups, aryl groups, arylalkyl groups, arylheteroalkyl groups, and/or sulfonic/carboxylic acid groups may be optionally substituted.

As used herein, the term "heteroalkyl" includes a straight chain or branched chain of carbon atoms, as well as mono or polycyclic carbon rings, containing at least one heteroatom and which may be optionally substituted. Examples of such heteroatoms include nitrogen, oxygen, phosphorus and sulfur. The heteroalkyl group is preferably a $C_1$-$C_{12}$ heteroaryl group, a $C_1$-$C_8$ heteroaryl group, a $C_1$-$C_6$ heteroaryl group, or a $C_1$-$C_4$ heteroaryl group. The same definition applies to the terms "heteroalkenyl" and "heteroalkynyl", with the exception that "heteroalkenyl" includes at least one carbon-carbon double bond, wherein "heteroalkynyl" includes at least one carbon-carbon triple bond.

Moreover, the term "aryl group" as used herein is not specifically restricted and includes mono-, bi- and polycyclic aryl groups, such as phenyl, naphthyl and anthracyl groups, which may be optionally substituted. The aryl group is preferably a $C_3$-$C_{24}$ aryl group, a $C_5$-$C_{18}$ aryl group or a $C_6$-$C_{12}$ aryl group.

Herein, the term "heteroaryl" is not specifically restricted and includes any mono-, bi- or polycyclic aryl group which further contains at least one heteroatom and which may be optionally substituted. The heteroaryl group is preferably a $C_3$-$C_{24}$ heteroaryl group, a $C_5$-$C_{18}$ heteroaryl group, or a $C_6$-$C_{12}$ heteroaryl group.

The term "amino acid" used herein is not specifically restricted and includes any natural and non-natural amino acids, as well as any compounds which contain at least one amino group and at least one carboxylic acid group, e.g. to form peptide bonds.

According to the present invention, each of $P_1$, $P_2$ and $P_3$ independently represents a single amino acid residue or a sequence of 2 or more amino acid residues, such as 2 to 36 amino acids residues, 4 to 30 amino acid residues or 6 to 24 amino acid residues connected by peptide bonds. The number of amino acid residues forming each of $P_1$, $P_2$ and $P_3$ may be the same or different. For example each of $P_1$ to $P_3$ may contain 3 amino acid residues, or $P_1$ may contain 2 amino acid residues and each of $P_2$ and $P_3$ may contain 3 or 4 amino acid residues.

Moreover, according to the present invention, the groups $P_1$, $P_2$ and $P_3$, for example taken together as -$P_1$-$P_2$-$P_3$-, may preferably form a single continuous peptide chain having a length of 6 to 78 amino acid residues, such as 8 to 48 amino acid residues, 10 to 36 amino acid residues, or 12 to 30 amino acid residues. In case $P_2$ is absent, each of P1 and P3 may be the same or different in length and/or sequence and, for example, contain a peptide chain having a length of 2 to 36 amino acid residues, 4 to 30 amino acid residues or 6 to 24 amino acid residues. In the present invention, one or more of $P_1$, $P_2$ and $P_3$ may contain only natural amino acids or may contain at least one non-natural amino acid, such as D-enantiomers of α-amino acids, or β-, γ-, or substituted amino acids, or amino acids with modified or isomerized side chains.

Herein, the expression "$P_1$ and $P_3$ are not bonded to each other" means that the terminal amino acids of each of $P_1$ and $P_3$ are not covalently connected. For example, the terminal amino acids of each of $P_1$ and $P_3$ may be characterized by a free amino group, an acylated or otherwise optionally substituted group, a free carboxylic acid group, an amidated or otherwise optionally substituted group, or salts/ions thereof.

In another embodiment of the peptidomimetic compounds as defined above, $R_1$ and $R_4$ are independently selected from H and a $C_1$-$C_6$ alkyl group, $R_2$ and $R_3$ are independently selected from a methyl group and an ethyl group, and X is —$CH_2CH_2CH_2$— or —$CF_2CF_2CF_2$—.

According to a specific embodiment of the present invention, in the above-defined peptidomimetic compounds, each of $R_1$ and $R_4$ is H, each of $R_2$ and $R_3$ is a methyl group, X is —$CH_2CH_2CH_2$— or —$CF_2CF_2CF_2$—, and each of $Y_1$ and $Y_2$ is S.

According to a specific embodiment of the present invention, in the above-defined peptidomimetic compounds, Q is C. According to another specific embodiment of the present invention, in the above-defined peptidomimetic compounds, Q is N, $R_6$ and $R_7$ are H, and $R_5$ is absent.

According to a specific embodiment of the present invention, the above-defined peptidomimetic compound is represented by the formulae GS-Sw (LF), GS-Sw (FP) and GS-Sw (PV) as depicted in claim 5.

In the present invention, the photo-switchable diarylethene fragment mimics two or more consecutive amino acid residues (preferably α-amino acid residues with uncharged side chains), so peptidomimetics possessing photo-controllable pharmaceutical and/or diagnostic activity can be obtained by incorporating the diarylethene fragments into prototype peptides or into other templates, including any known natural or artificial pharmaceutically, prophylactically and/or diagnostically active peptides, in place of one or several natural unpolar amino acid residues. These residues should preferably be, but are not limited to, part of a peptide backbone conformational turn (alpha-, beta- gamma-, delta-, etc.) because in such a case the structure of the photo-switchable diarylethene fragment (in either "open" or "closed" form) can be aligned with the template.

Importantly, one of the photo-switchable diarylethene forms ("closed" or "open") will be better matched to the template backbone in its biologically active conformation, so the resulting peptidomimetic structure and biological activity is closely retained when the incorporated fragment exists in this form. Irradiation of the resulting peptidomimetic with light of the wavelength optimal for photo-isomerization of the fragment thus results in significant changes in the overall structure and conformational flexibility of the peptidomimetic, and, correspondingly, its pharmaceutical and/or diagnostic activity. By the action of the light of another wavelength the diarylethene photo-switchable unit can isomerize back to the initial form (cf. the above Schemes 2 and 3). The structure and thus the pharmaceutical and/or diagnostic activity of the peptidomimetic can be restored in this way.

According to the present invention, the photo-isomerization can be performed back and forth many times, without photo-destruction of the diarylethene fragment. The "closed" and "open" forms of the peptidomimetic are stable in the temperature interval optimal for most living organisms (i.e. in a range of 0 to 70° C.), so they can be used as pharmaceutical, prophylactic or diagnostic agents in the corresponding form, which will remain unchanged until the photo-isomerization is triggered by local exposure to light of a suitable wavelength.

Based on this advantageously flexible system, it is possible to specifically treat or diagnose a desired body fragment, localized tissue, tissue region, or bodily fluid by administering the peptidomimetic of the present invention in its inactive form and by irradiating the respective region in the patient with light of the suitable wavelength for isomerizing the peptidomimetic into its active form.

According to a further aspect, the present invention provides an intermediate compound represented by the general formula II or a salt thereof, usable for the synthesis of the peptidomimetic compound as described above:

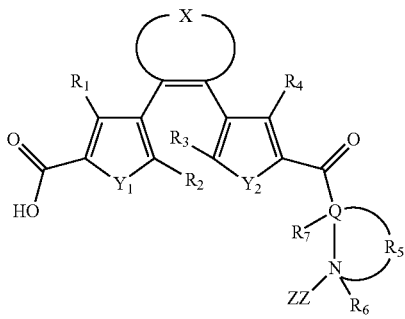

wherein
ZZ represents a protecting group;
$R_1$ and $R_4$ are independently selected from the group consisting of H, an alkyl group, alkenyl group, alkynyl group, alkoxy group, aryl group, heteroaryl group, cyano group, nitro group, phosphate group and sulfoxyl group;
$R_2$ and $R_3$ are independently selected from the group consisting of an alkyl group, alkenyl group, alkynyl group, alkoxy group, aryl group, heteroaryl group, cyano group, nitro group, phosphate group and sulfoxyl group;
X represents —$(CH_xF_y)_z$—, wherein x+y=2, x=0, 1 or 2, y=0, 1 or 2 and z=2 to 4;
$Y_1$ and $Y_2$ are independently selected from S, $SO_2$, N, N-alkyl, or O;
Q is C or N;
$R_5$ is selected from H, an alkyl group, heteroalkyl group, alkenyl group, heteroalkenyl group, alkynyl group or a heteroalkynyl group, and is bound to Q or may form a ring together with Q and N, or $R_5$ is absent;
$R_6$ is selected from H, an alkyl group, heteroalkyl group, alkenyl group, heteroalkenyl group, alkynyl group, heteroalkynyl group, alkoxy group, aryl group, and heteroaryl group, or is absent; and
$R_7$ is selected from H, an amino acid side chain, an alkyl group, heteroalkyl group, alkenyl group, heteroalkenyl group, alkynyl group, heteroalkynyl group, alkoxy group, aryl group or a heteroaryl group;
with the proviso that when Q is N, $R_5$ is absent, and
with the proviso that when $R_5$ forms a ring together with Q and N, $R_6$ is absent.

According to the present invention, the intermediate compound of formula II further includes all possible stereo- and regioisomers with regard to groups $R_5$, $R_6$, $R_7$ and Q.

According to a further embodiment, the present invention also relates to the above-defined intermediate compound in its closed form. In such a case, said intermediate compound also includes, in addition to those mentioned above for the open form, all possible stereo- and regioisomers with regard to $R_2$ and $R_3$.

If not expressly stated elsewise, all definitions provided above, including the specific embodiments of $R_1$ to $R_4$, X, $Y_1$ and $Y_2$, Q, and $R_5$ to $R_7$ also apply to the intermediate compound of the present invention.

In another embodiment of the intermediate compound as defined above, ZZ is selected from t-butyloxycarbonyl (Boc) and fluorenylmethoxycarbonyl (Fmoc).

According to a further embodiment of the present invention, in the intermediate compound as defined above, $R_1$ and $R_4$ are independently selected from H and a $C_1$-$C_6$ alkyl group, $R_2$ and $R_3$ are independently selected from a methyl group and an ethyl group and X is —$CH_2CH_2CH_2$— or —$CF_2CF_2CF_2$—.

According to a further embodiment of the present invention, in the above-defined intermediate compound, each of $R_1$ and $R_4$ is H, each of $R_2$ and $R_3$ is a methyl group, X is —$CH_2CH_2CH_2$— or —$CF_2CF_2CF_2$—, and each of $Y_1$ and $Y_2$ is S.

According to a yet further embodiment of the present invention, in the above-defined intermediate compound, Q is N, and $R_5$ is absent. Accordingly, said compound is represented by the following formula II-1:

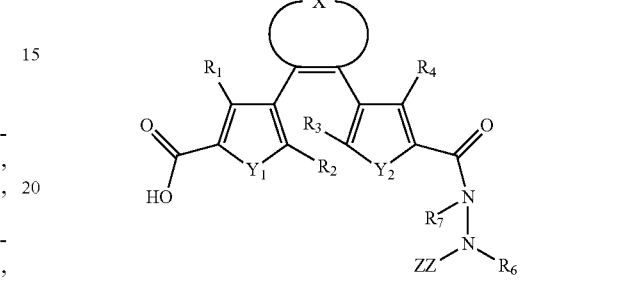

According to a further embodiment of the present invention, in the above-defined intermediate compound, Q is C. Accordingly, said compound is represented by the following formula II-2:

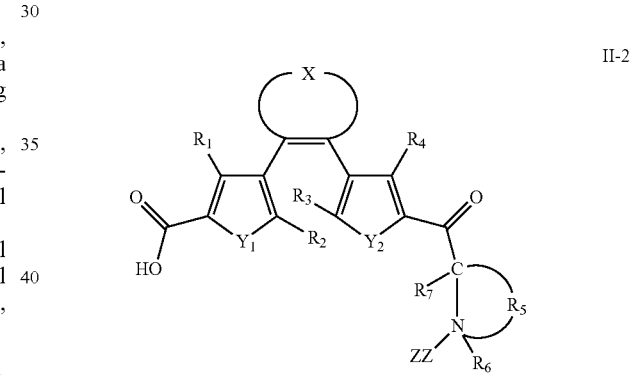

Particularly preferred examples of respective compounds of general formula II-2 are shown in FIG. 6 (compounds 4a, 4b, and 4c).

The intermediate compound II (including e.g. compounds II-1 and II-2) is sometimes also referred to as "building block" and is designed to replace one or more natural or non-natural amino acids within a cyclic or linear polypeptide chain, and contains the photo-switchable diarylethene fragment, which can exist in the "open" or "closed" form that are interconvertible by light of different wavelengths (also cf. the above Schemes 2 and 3).

Such a building block is specifically advantageous in that the amino group therein is e.g. mimicked by a carboxylic acid hydrazide fragment (Q=N, $R_5$=absent, $R_6$ and $R_7$=H) that ensures compatibility with peptide synthesis. The building block may then be incorporated into the peptidomimetic backbones. e.g. by standard peptide synthesis protocols, such as Fmoc or Boc solid-phase peptide synthesis.

The photo-switchable diarylethene fragment may be the "open" or "closed" form during the synthesis, for example depending on what is more appropriate to achieve better chemical yields of the peptidomimetics.

In the preferred case that in intermediate compound II, Q is C (cf. the above formula II-2), as well as in the preferred case that in compounds Ia and Ib of the present invention Q is C, said compounds may preferably contain an α-amino acid residue (Q=C, R$_7$=amino acid side chain), as follows:

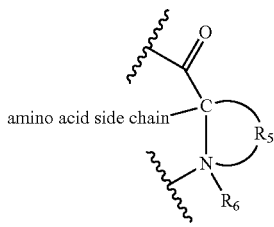

As mentioned above, when R$_7$ represent an amino acid side chain the linker group may form an amino acid, which can be effectively used in the synthesis of the peptidomimetic compounds of the present invention.

In particular, respective compounds are advantageously characterized by an increased stability of the photoswitch of the present invention and may be more readily used in standard methods of solid-phase peptide synthesis. Moreover, it is also possible to adjust the appropriate geometry of the N-terminus of the intermediate compound II-2 by varying the α-amino acid residue. Most importantly, since the α-amino acid, in place of the hydrazide, can be selected to be part of the target polypeptide sequence (e.g. P3), the effective size of the photo controlling element foreign to the target polypeptide can be reduced down to the molecular photo-switchable system (see Scheme 3), and compatibility of the artificial controlling element with the target polypeptide is enhanced.

In a further aspect, the present invention provides a method of manufacturing the intermediate compound II-1 or a salt thereof, represented by the above-defined general formula II, wherein Q is N, R$_6$ and R$_7$ is H, and R$_5$ is absent

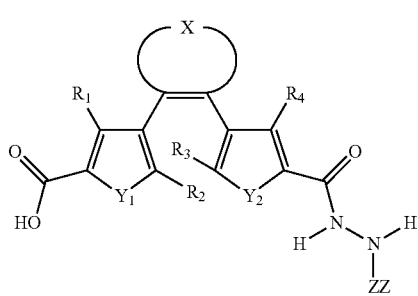

wherein
ZZ represents a protecting group;
R$_1$ and R$_4$ are independently selected from the group consisting of H, an alkyl group, alkenyl group, alkynyl group, alkoxy group, aryl group, heteroaryl group, cyano group, nitro group, phosphate group and sulfoxyl group;
R$_2$ and R$_3$ are independently selected from the group consisting of an alkyl group, alkenyl group, alkynyl group, alkoxy group, aryl group, heteroaryl group, cyano group, nitro group, phosphate group and sulfoxyl group;
X represents —(CH$_x$F$_y$)$_z$—, wherein x+y=2, x=0, 1 or 2, y=0, 1 or 2 and z=2 to 4; and Y$_1$ and Y$_2$ are independently selected from S, SO$_2$, N, N-alkyl, or O;
comprising the steps of
a) dissolving a dicarboxylic acid compound represented by the general formula III-1, a coupling reagent, a base and ZZ-hydrazine in a solvent;

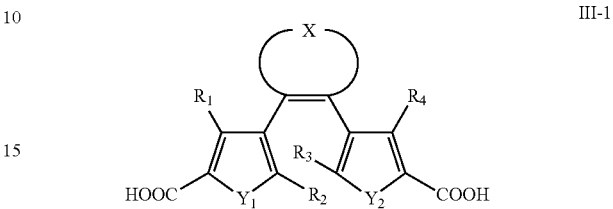

wherein each of R$_1$ to R$_4$, X, Y$_1$ and Y$_2$ is as defined above;
b) stirring the mixture for 30 minutes to 24 hours;
c) pouring the mixture into excess of water to obtain a compound of the above formula II-1 or a salt thereof as a precipitate; and
d) optionally dissolving the precipitate in an organic solvent and washing the solution with aqueous sodium bicarbonate and hydrogen chloride solutions.

According to a further embodiment, the method for manufacturing the intermediate compound as defined above may further include a step (e) of evaporating the solvent and drying the product.

According to a further embodiment, the present invention also relates to the above-defined method for manufacturing the intermediate compound as defined above in its closed form.

If not expressly stated elsewhere, all definitions provided above, including the specific embodiments of R$_1$ to R$_4$, X, Y$_1$ and Y$_2$, Q, and R$_5$ to R$_7$ also apply to the method of manufacturing the intermediate compound of the present invention.

In another embodiment in the method as defined above, the solvent is selected from dimethylformamide, dimethylsulfoxide, hexamethylphosphotriamide; and/or the protecting group is selected from t-butyloxycarbonyl (Boc) and fluorenylmethoxycarbonyl (Fmoc); and/or the coupling reagent is selected from the group consisting of carbodiimides, N,N,N',N'-Tetramethyl-O-(benzotriazol-1-yl)uronium tetrafluoroborate (TBTU), 2-(1H-Benzotriazole-1-yl)-1,1,3,3-tetramethyluronium hexafluorophosphate (HBTU), 1-[Bis(dimethylamino)methylene]-1H-1,2,3-triazolo[4,5-b]pyridinium 3-oxid hexafluorophosphate (HATU) and (Benzotriazol-1-yloxy)tripyrrolidinophosphonium hexafluorophosphate (PyBop); and/or the base is selected from triethylamine and diisopropylethylamine.

In a further aspect, the present invention provides a use of a photo-switchable molecular system represented by the following scheme including general formulae IVa and IVb, as a fragment in a pharmaceutically and/or diagnostically active compound, which allows to toggle between an activated and deactivated state thereof

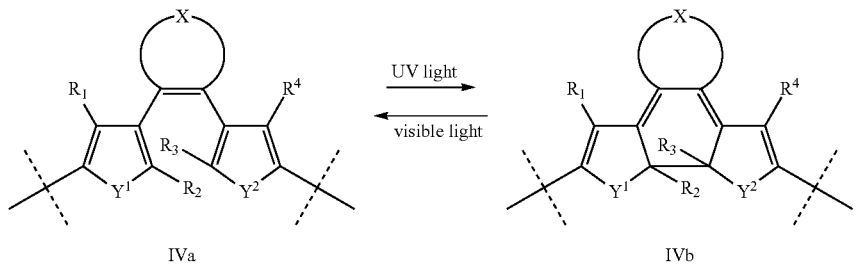

IVa          IVb wherein
$R_1$ and $R_4$ are independently selected from the group consisting of H, an alkyl group, alkenyl group, alkynyl group, alkoxy group, aryl group, heteroaryl group, cyano group, nitro group, phosphate group and sulfoxyl group;
$R_2$ and $R_3$ are independently selected from the group consisting of an alkyl group, alkenyl group, alkynyl group, alkoxy group, aryl group, heteroaryl group, cyano group, nitro group, phosphate group and sulfoxyl group;
X represents —$(CH_xF_y)_z$—, wherein x+y=2, x=0, 1 or 2, y=0, 1 or 2 and z=2 to 4;
$Y_1$ and $Y_2$ are independently selected from S, $SO_2$, N, N-alkyl, or O.

If not expressly stated elsewhere, all definitions provided above, including the specific embodiments of $R_1$ to $R_4$, X, $Y_1$ and $Y_2$ also apply to the photo-switchable molecular system of the present invention.

A further aspect of the present invention relates to the peptidomimetic compound according to the present invention for use in medicine. Preferably, the peptidomimetic compound according to the present invention is used in photodynamic therapy for treating a localized disorder, i.e. a disorder restricted to a specific region in the patient.

Herein, the term "patient" is not specifically restricted and generally includes any animal, particularly a human being who is receiving a medical treatment.

Further, the present invention relates to the peptidomimetic compound as defined above for use in a method for treating disorders selected from viral, bacterial, parasitic or fungal infection, inflammation, wounds, hemorrhages, hyperplastic, neoplastic, sclerotic, thrombotic or necrotic disorders.

In a further embodiment, the present invention relates to a pharmaceutical composition comprising the peptidomimetic compound as defined above, and optionally one or more adjuvants, diluents or other auxiliary agents.

The above-defined peptidomimetic compound or pharmaceutical composition may be formulated in any desired form such as tablets, solutions, gels, sprays (aerosols) and ointments. Depending on the formulation form and the disease, the compound or the pharmaceutical composition may be administered, for example, via oral, topical, intravenous, intramuscular, peritoneal, nasal or subcutaneous route, etc.

The dosage of the peptidomimetic compound according to the present invention may depend on the nature of the peptidomimetic compound, the symptoms, state (e.g. immunosuppression or hyperreactivity) or age of a patient, the type of administration, etc. Suitable dosages may be determined by a person skilled in the art.

The present invention also relates to a method of treatment, wherein the peptidomimetic compound of the present invention is administered to a patient for treating disorders selected from viral, bacterial, parasitic or fungal, infection, inflammation, wounds, hemorrhages, hyperplastic, neoplastic, sclerotic, thrombotic or necrotic disorders.

THE FIGURES SHOW

Figure 5:
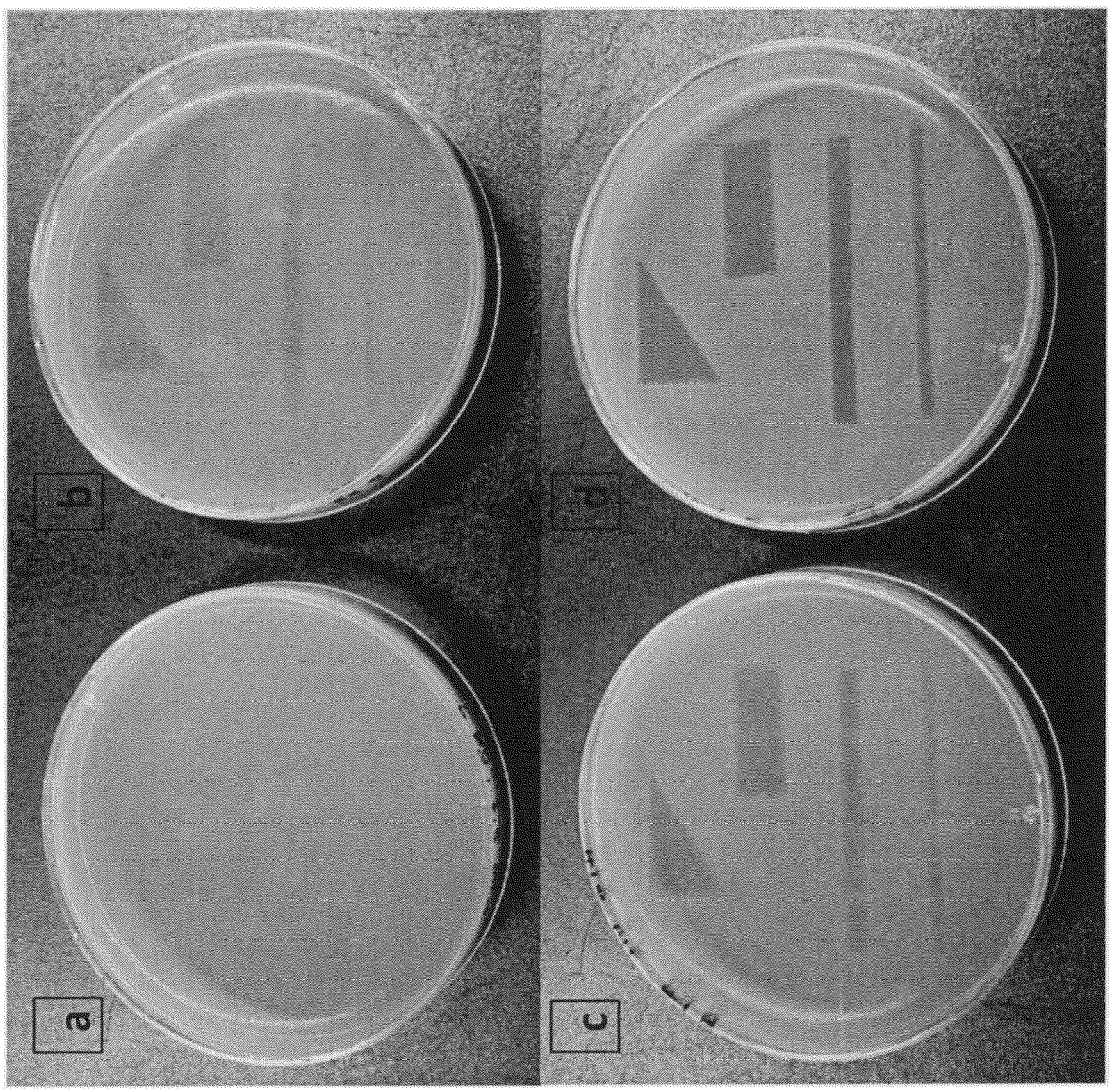

FIG. 5 shows an antimicrobial effect of the peptidomimetic GS-SwFP in the "open" form on *Staphylococcus xylosus* growth. The compound was applied to the bacterial lawn at different concentrations and then irradiated by visible light. Some geometrical shapes were cut out from a paper covering the entire Petri dish, such that the photo-switchable compound was converted into the "open" form only in those small areas exposed to the light. (A) 6 μg/ml of the "closed" form were converted into the "open" form by about 60% (as calculated from the curve on FIG. 2 and described in example 3); (B) 6 μg/ml, converted to 80%; (C) 8 μg/ml, converted to 60%; (D) 8 μg/ml, converted to 80%; Where the photo-switchable GS analogue is successfully activated, it exhibits a pronounced antimicrobial activity as seen from the transparent areas, where no bacterial growth in observed upon incubation at 37° C. for 18 hours.

Figure 6:
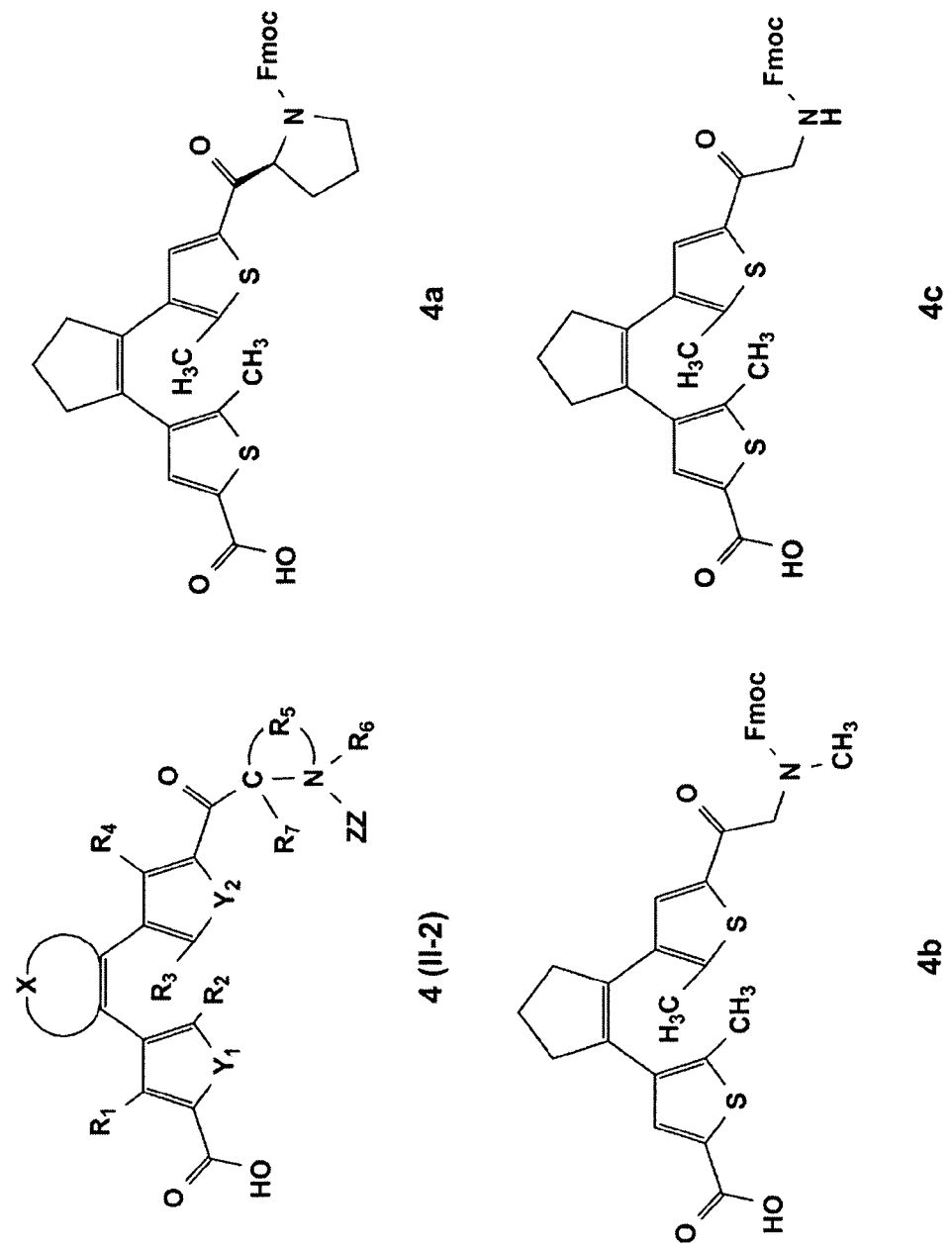

FIG. 6 shows intermediate compound II-2 (compound 4), and particularly preferred examples thereof (compounds 4a, 4b, 4c). Compound 4a contains a residue of L-proline and is an example of the building block with the amino acid fragment that contains a cyclic aliphatic ring; compound 4b contains a residue of N-methyl glycine and is an example of the photoswitching building block with N-substituted amino acid fragment; compound 4c contains a residue of glycine (amino acid side chain=H) and is the closest example to the building block where the —NH— fragment is substituted by —$CH_2$—.

Figure 7:
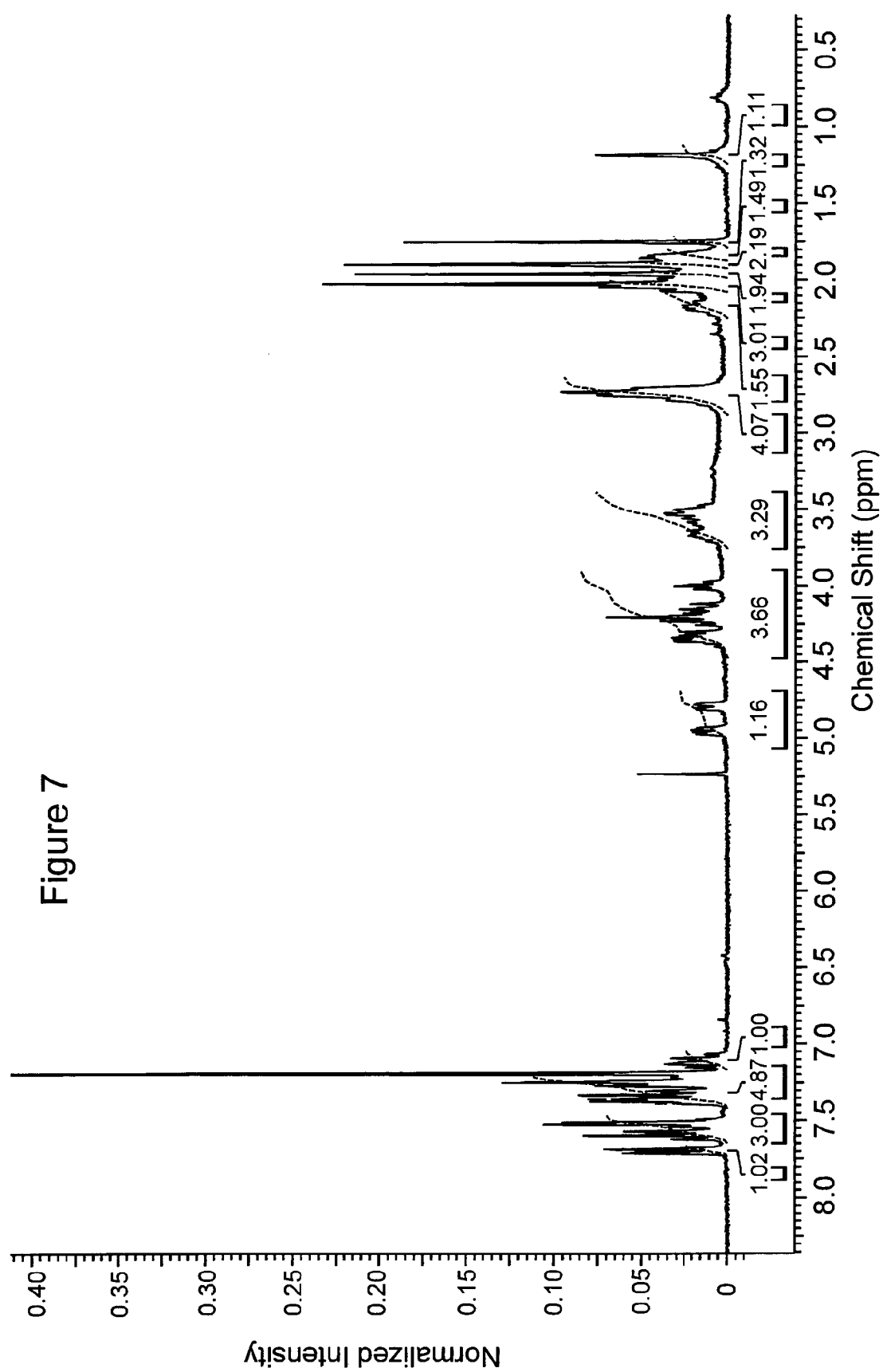
Figure 8:
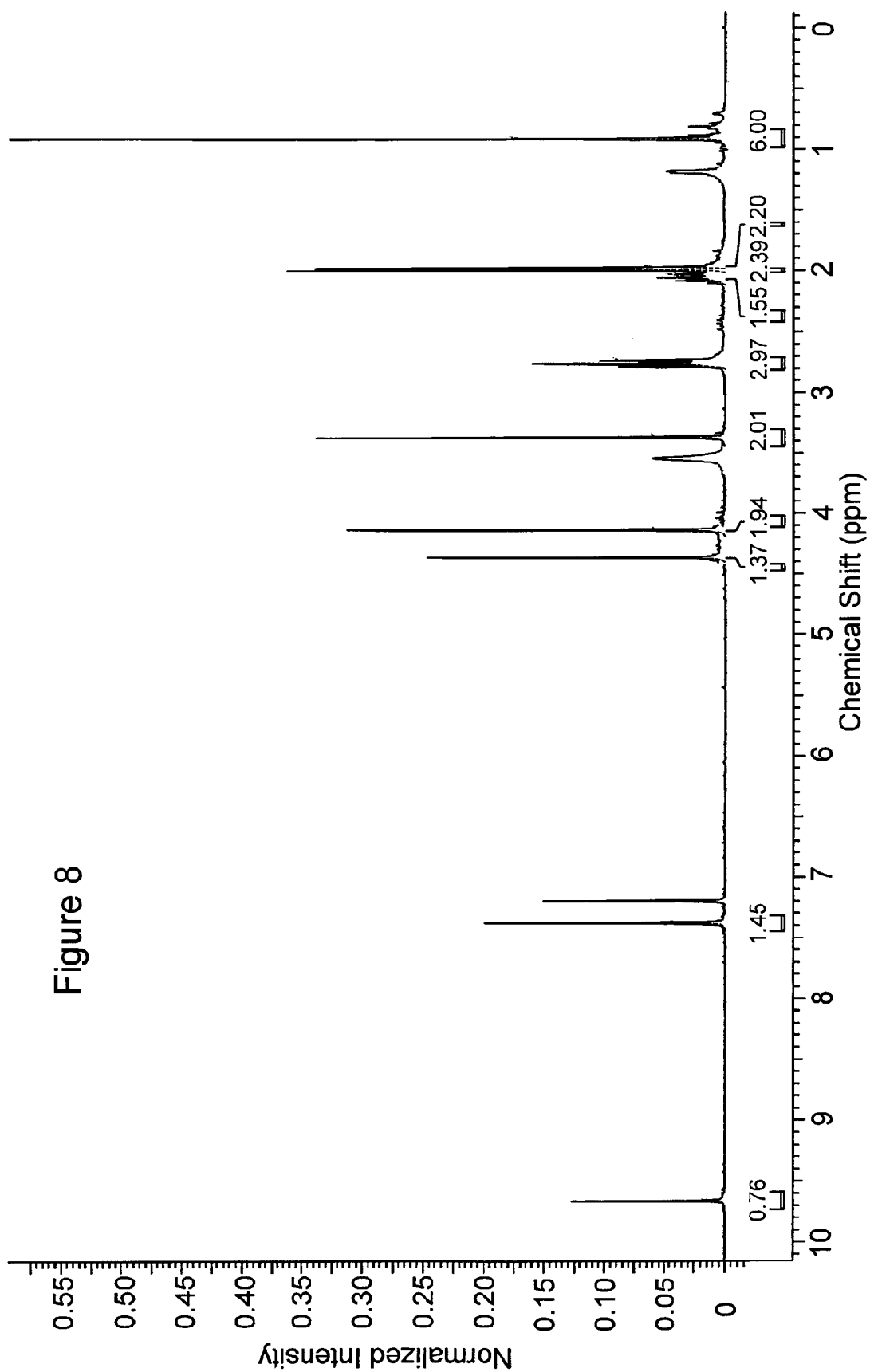
Figure 9:
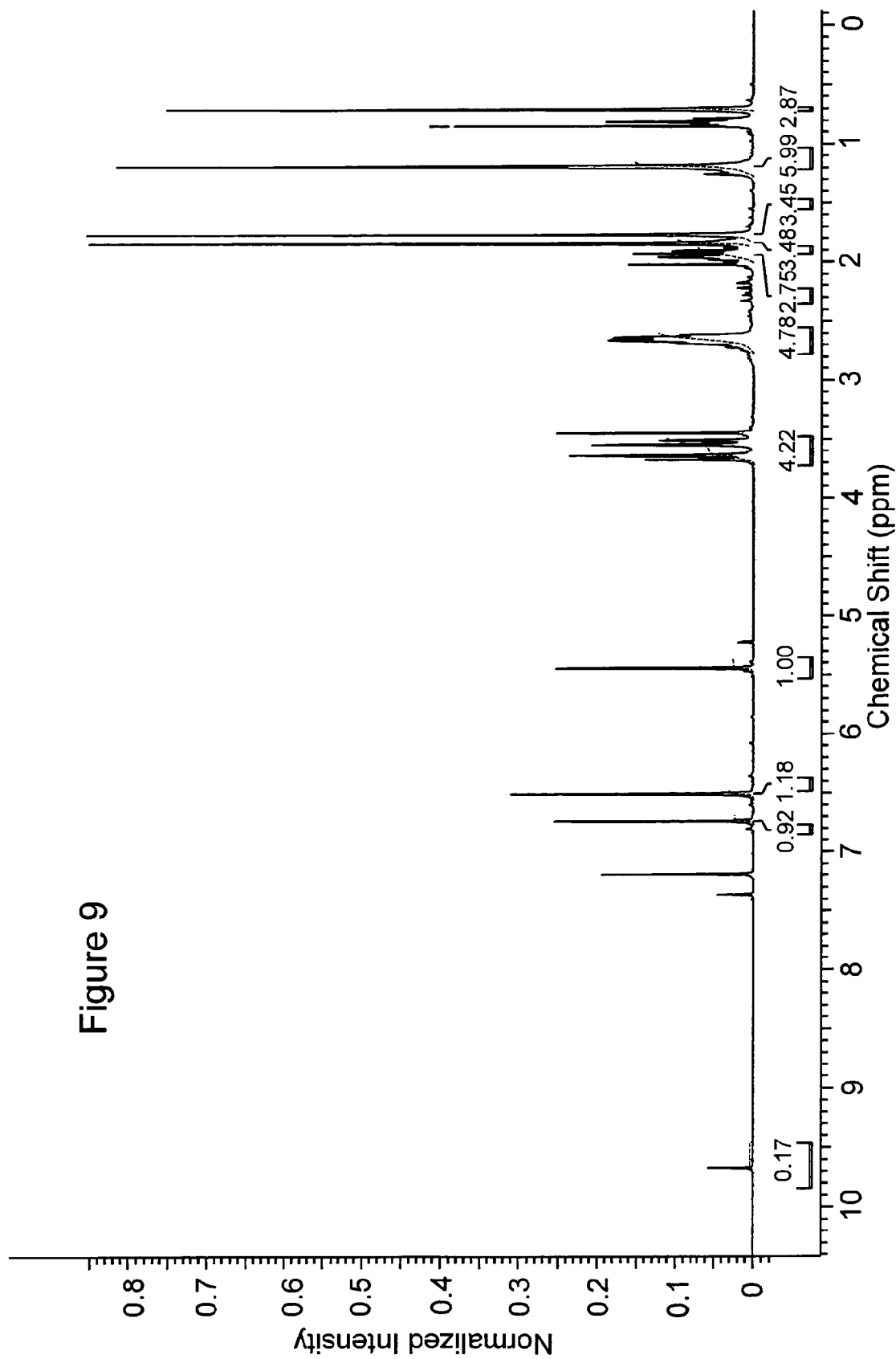
Figure 10:
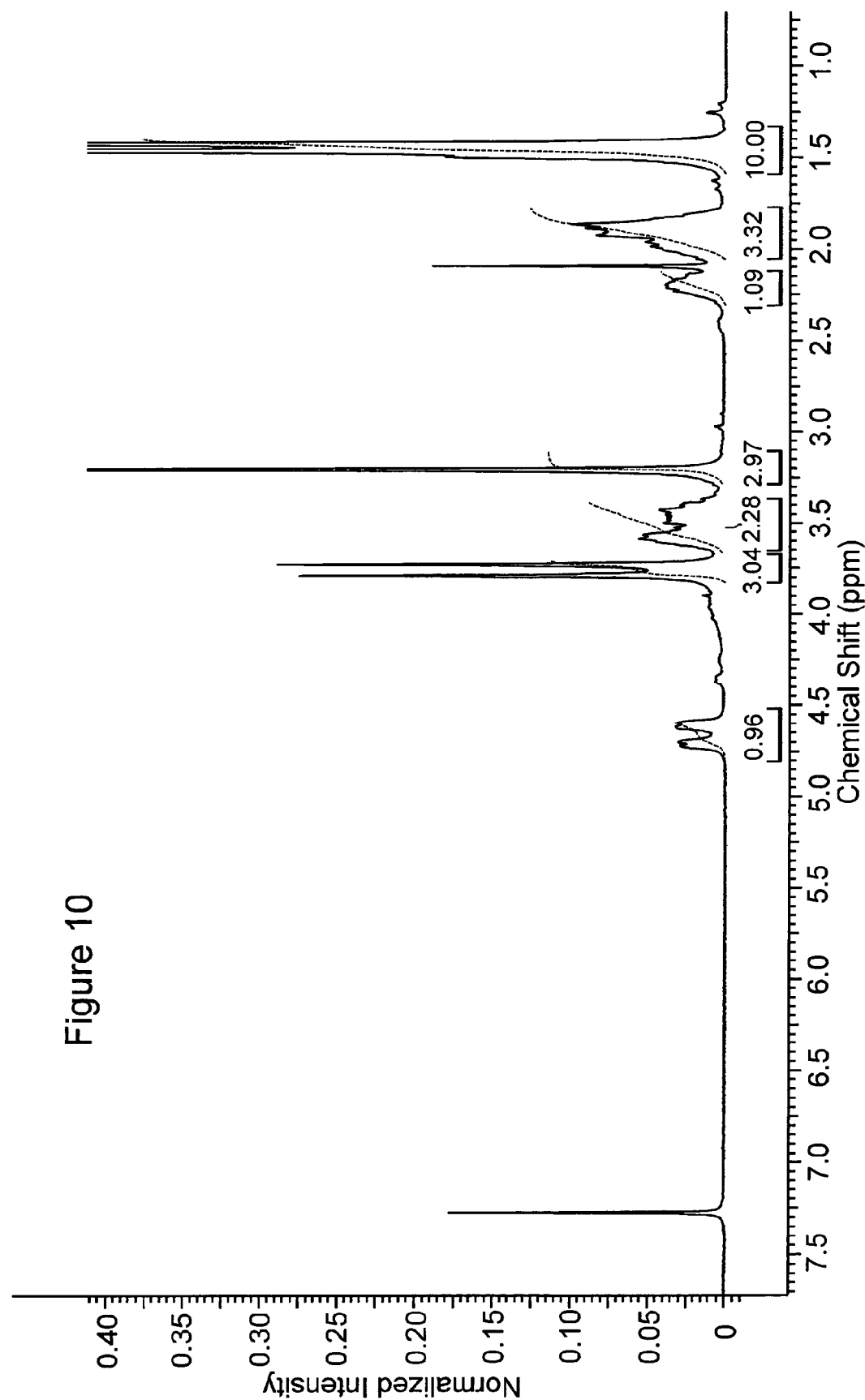

FIG. 7 shows the $^1$H NMR spectrum of compound 4a.
FIG. 8 shows the $^1$H NMR spectrum of compound 14.
FIG. 9 shows the $^1$H NMR spectrum of compound 7.
FIG. 10 shows the $^1$H NMR spectrum of compound 8.

The peptidomimetic compounds of the present invention are chemically and thermally stable and reversibly transform between their biologically active and inactive (or less active)

forms in high conversion efficiency through irradiation of light having suitable wavelengths. Furthermore, the peptidomimetic compounds of the present invention are biocompatible and resistant to photo-destruction and proteases. Consequently, the pharmaceutical and/or diagnostic activity of the peptidomimetics of the present invention may be effectively switched "on" and "off", which renders the peptidomimetic compounds of the present invention particularly advantageous in the specific treatment of localized disorders in a patient. By only activating the pharmaceutical and/or diagnostic properties of the peptidomimetic at the desired site of action (and deactivating outside that area), side-effects are reduced and the therapeutic index is significantly increased. Particularly, the peptidomimetic compounds of the present invention may be readily employed in a variety of established applications, including photodynamic therapy.

In addition, the intermediate compound of the present invention easily allows to readily prepare a large variety of peptidomimetic compounds, e.g. using natural peptides as templates. Synthesis of such peptidomimetics is simple and can be achieved by using standard methods such as convergent synthesis, parallel synthesis, automated solid-phase synthesis, etc.

In the following, the present invention is further illustrated by the following examples, but is not limited thereby.

EXAMPLE 1

Synthesis of the Photo-Switchable Building Block (1b)

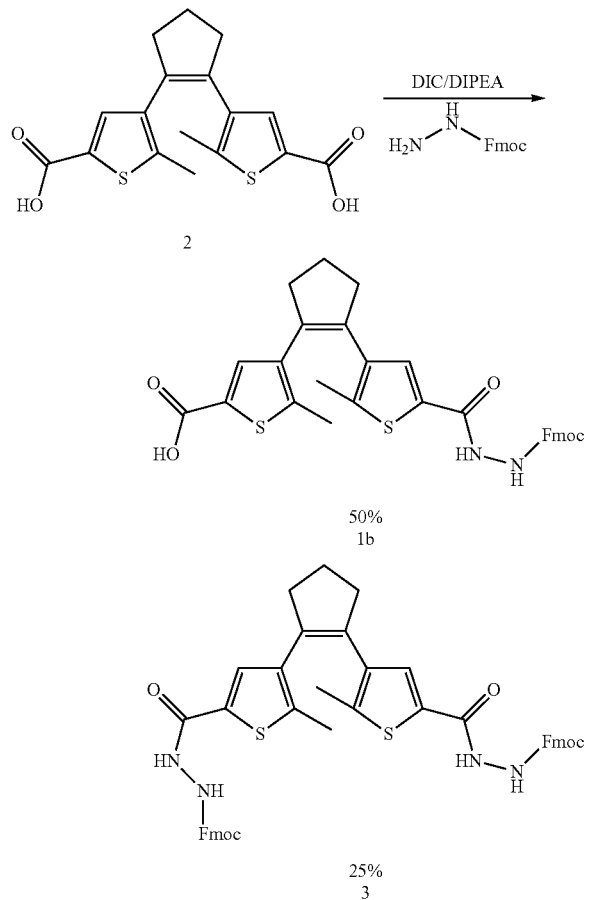

The starting dicarboxylic acid 2 used for the synthesis of Ib was obtained as described in the literature [S. Gronowitz, K. Stenhamar, L. Svensson, *Heterocycles* 1981, 15, 947; T. B. Norsten, N. R. Branda, *J. Am. Chem. Soc.* 2001, 123, 1784].

Compound 2 (5 g, 14.3 mmol) was dissolved in dimethylformamide (25 ml). N,N-diisopropylcarbodiimide (DIC, 1.76 g, 14 mmol) and subsequently N,N-diisopropylethylamine (DIPEA, 3.7 g, 28.6 mmol) were added to the solution. Fmoc-hydrazine (Fmoc-NH—$NH_2$; 3.56 g; 14 mmol) was added immediately. After stirring the reaction mixture overnight it was poured into water (100 ml). The precipitate was filtered, dissolved in dichloromethane (200 ml) and washed twice with 0.5 M aq solution of sodium bicarbonate (100 ml), then with 0.5 M aq solution of hydrochloric acid (100 ml) in order to remove the unreacted dicarboxylic acid.

The organic phase was dried with magnesium sulfate. Evaporation of dichloromethane under reduced pressure gave the crude material which contained, along with the desirable 1 b, also the by-product 3. The by-product did not interfere with the solid-phase peptide synthesis, so the obtained material was used without additional purification. The analytically pure 1 b can be obtained using RP-HPLC (acetonitrile/water mixture as the eluent).

$^1$H-NMR (500 MHz, DMSO-$d_6$), $\delta$=1.90 (s, 3H, $CH_3$), 1.94 (s, 3H, $CH_3$), 1.95-2.05 (m, 2H), 2.79 (t, J=7.8 Hz, 4H), 4.2-4.4 (system $CH_2CH$, two rotamers 4:1), 7.17-7.91 (m, aromatic protons, 10H), 9.00-9.36 (rotamers 1:4, 1H), 10.22-10.46 (rotamers 4:1, 1H).

EXAMPLE 2

Synthesis and Isolation of GS Analogues (General Procedure)

Synthesis of GS analogues: cyclo($^D$FPVO-1b-PVOL), cyclo($^D$FPVOL-1b-VOL) and cyclo($^D$FPVOL$^D$F-1b-OL) (GS-Sw(LF), GS-Sw(FP), GS-Sw(PV)).

Figure 1:
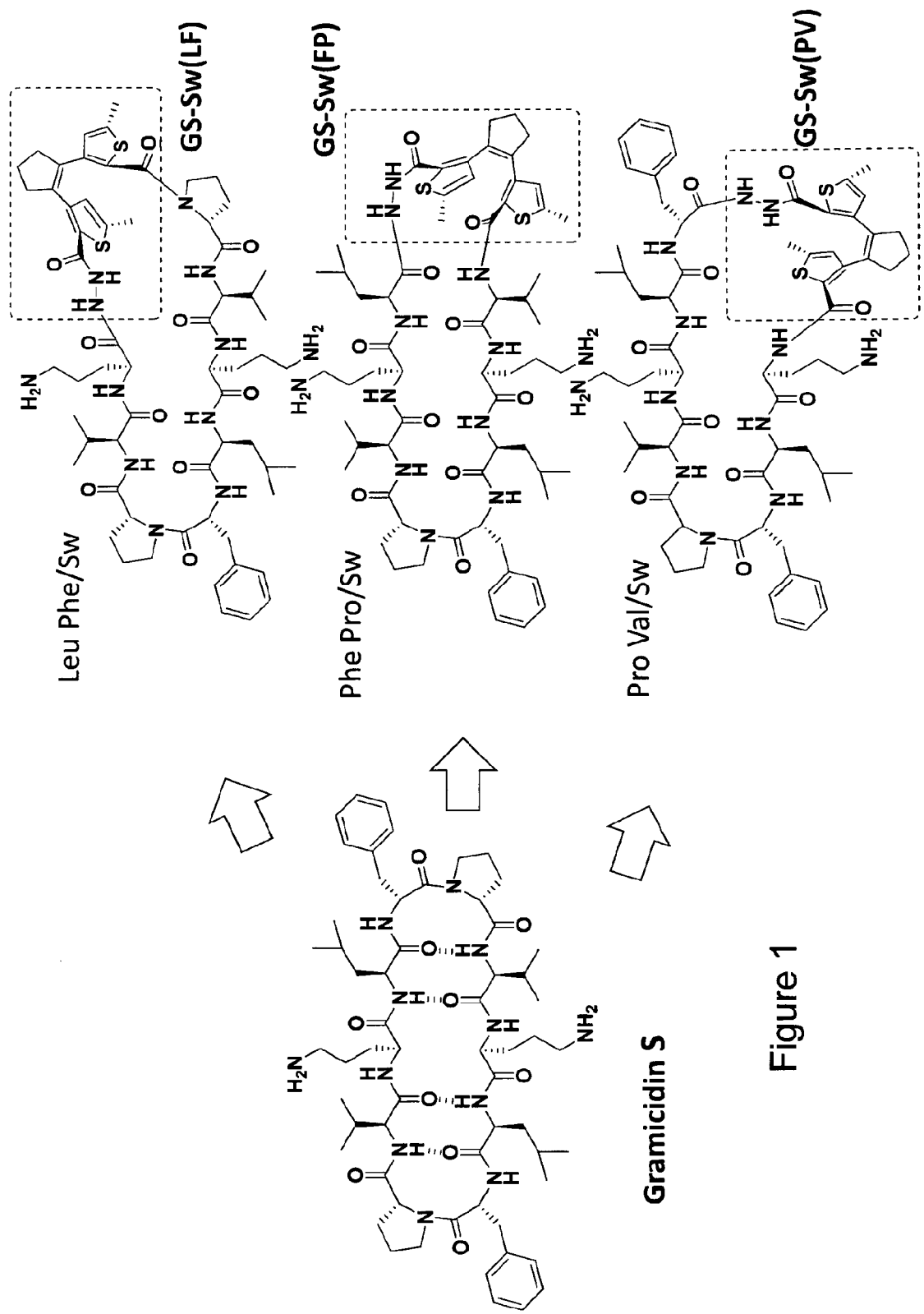
FIG. 1 shows the cyclic antibiotic Gramicidin S (GS), and three photo-sensitive peptidomimetics derived from it. The GS analogues are shown in their "open" forms.

The known peptide antibiotic Gramicidin S (GS) was used as a template. This cyclic decapeptide is known to exist in an antiparallel β-sheet with the strands fixed by two β-turns ([PVOL$^D$FPVOL$^D$F]$_{cyclo}$, with O=ornithine, and $^D$F=D-phenylalanine). Four hydrogen bonds stabilize the overall amphipatic conformation of the molecule (cf. FIG. 1). GS is strongly membrane-active against Gram-positive bacteria, but has some undesirable hemolytic side-effects on red blood cells, and it is significantly protease-resistant. The unpolar diarylethene photo-switchable fragment in the "open"-form is well suited to replace the unpolar dipeptide units in one of the β-turns, either L$^D$F, $^D$FP, or PV, thereby giving the respective peptidomimetics GS-Sw(LF), GS-Sw(FP), and GS-Sw(PV) (also cf. FIG. 1).

Standard Fmoc-based solid-phase synthesis and commercially available reagents were used for the synthesis of all the GS analogues. $^D$Phenylalanine pre-loaded chlorotrityl resin with loading of 0.73 mmol/g (200 mg, 1 equiv) was used to synthesize the linear precursors. Coupling of the amino acid was performed using the following molar ratios of the reagents: Fmoc-amino acid (4 equiv), HOBt (4 equiv), HBTU (3.9 equiv), DIPEA (8 equiv). Incorporation of the diarylethene building block was performed by coupling with 1 b (in the form of the crude mixture as obtained in example 1 above; the amount was taken to provide 1.5 equiv of 1 b, the photo-switchable fragment in the "open" form), HOBt (1.5 equiv), HBTU (1.45 equiv.), DIPEA (3 equiv). The coupling time in all cases was 1 hour. N-Fmoc-deprotection was carried out by treating the resin with 20% piperidine in DMF for min. After completing the synthesis, the resin was washed with dichloromethane and dried under vacuum for 24 h. The linear precursors were cleaved from the resin by a mixture of hexafluoroisopropanol and dichloromethane (1:3) (maintaining the side chain protection of ornithine residues). The volatile products from the filtered solution were blown off by argon flow. After dissolving the residue in an acetonitrile-water (1:1) mixture and subsequent lyophilization, the crude linear precursors were obtained and used for the cyclization without further purification. The conversion of the linear precursors into the targeted cyclic peptidomimetics was done in dichloromethane (1 L, the precursor did not dissolve completely) by addition solution of PyBOP (3 equiv) and HOBt (3 equiv) in dimethylformamide (1 ml) followed by DIPEA (6 equiv) to the suspension of the corresponding precursor. The reaction mixture was stirred for 8 h and additional amounts (the same as above) of the reagents (PyBOP, HOBt, DIPEA) were added. After 16 h, the solvent was evaporated under reduced pressure and the residue was lyophilized. The deprotection cocktail (trifluoroacetic acid, triisopropylsilane and water, 92.5:2.5:5 by volume, 10 ml) was added to the residue. After 15 min, the volatiles were blown off by argon flow and the residue was lyophilized.

The crude cyclic peptidomimetics were purified using RP-HPLC in two steps: first on a preparative C18 column (Vydac®, 22×250 mm) with a linear A:B gradient of 8% B/min and 17 ml/min flow rate, followed by the second step on a C18 semipreparative column (Vydac®, 10×250 mm) with a linear A:B gradient of 4% B/min and a 6 ml/min flow rate, where A is a mixture of 10% acetonitrile and 90% of the 5 mM HCl; B is a mixture of 90% acetonitrile and 10% of the 5 mM HCl. The purity of the peptidomimetics was checked on the analytical C18 column (Vydac®, 4.6×250 mm) with a linear A:B gradient of 1% B/min and a 1.5 ml/min flow rate. The identity of each peptidomimetic was confirmed by MALDI-TOF mass spectrometry; m/z=1225.4 [GS-Sw(LF)], 1241.5 [GS-Sw(FP)], 1289.5 [GS-Sw(PV)].

EXAMPLE 3

Characterization of Photochromic Properties of the GS Analogues

Each of the GS analogues was tested for photo-conversion efficiency from the more flexible state of the diarylethene unit ("open" form) to the rigid state ("closed" form) upon irradiation by UV light. Solutions of each peptidomimetic, GS-Sw(LF), GS-Sw(FP), and GS-Sw(PV), were prepared with a concentration of 100 µg/ml (in a water-acetonitrile mixture, 3:1). Then the extent of conversion from the "open" state to the "closed" state upon irradiation by UV light was determined using RP-HPLC (analytical C18 column, linear A:B gradient of 4% B/min, 1.5 ml/min flow rate) after 0, 5, 25, 50 and 75 min of light exposition. A standard short-wavelength UV lamp (Spectroline®XX-15F/F) was used, and the solutions were placed in 10 cm distance from the lamp at 25° C.

Figure 2:
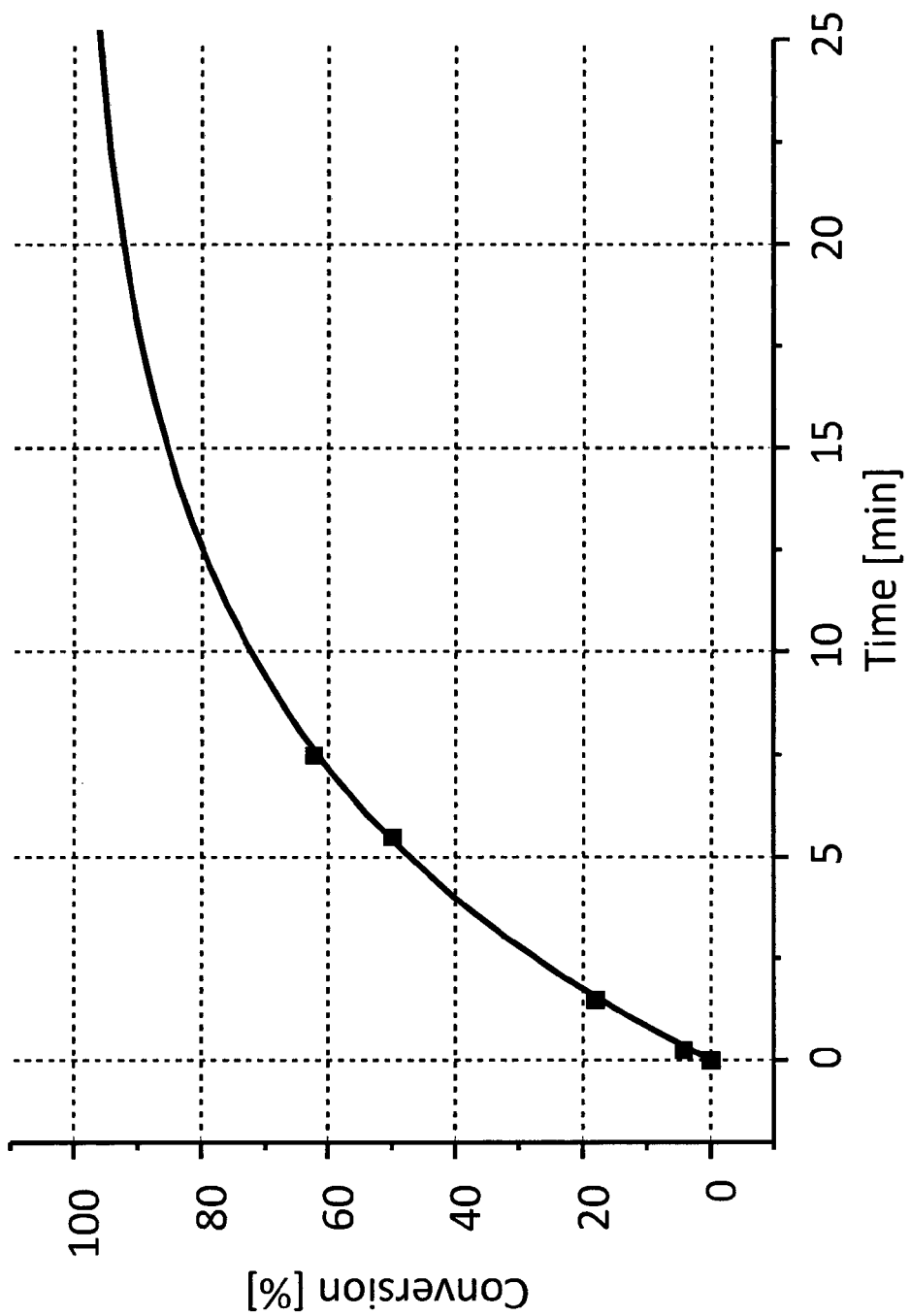
FIG. 2 shows kinetics of the photo-conversion of GS-Sw (FP) from its "closed" to its "open" form in a water-acetonitrile mixture, 3:1, at 25° C., 100 μg/ml concentration.
Figure 3:
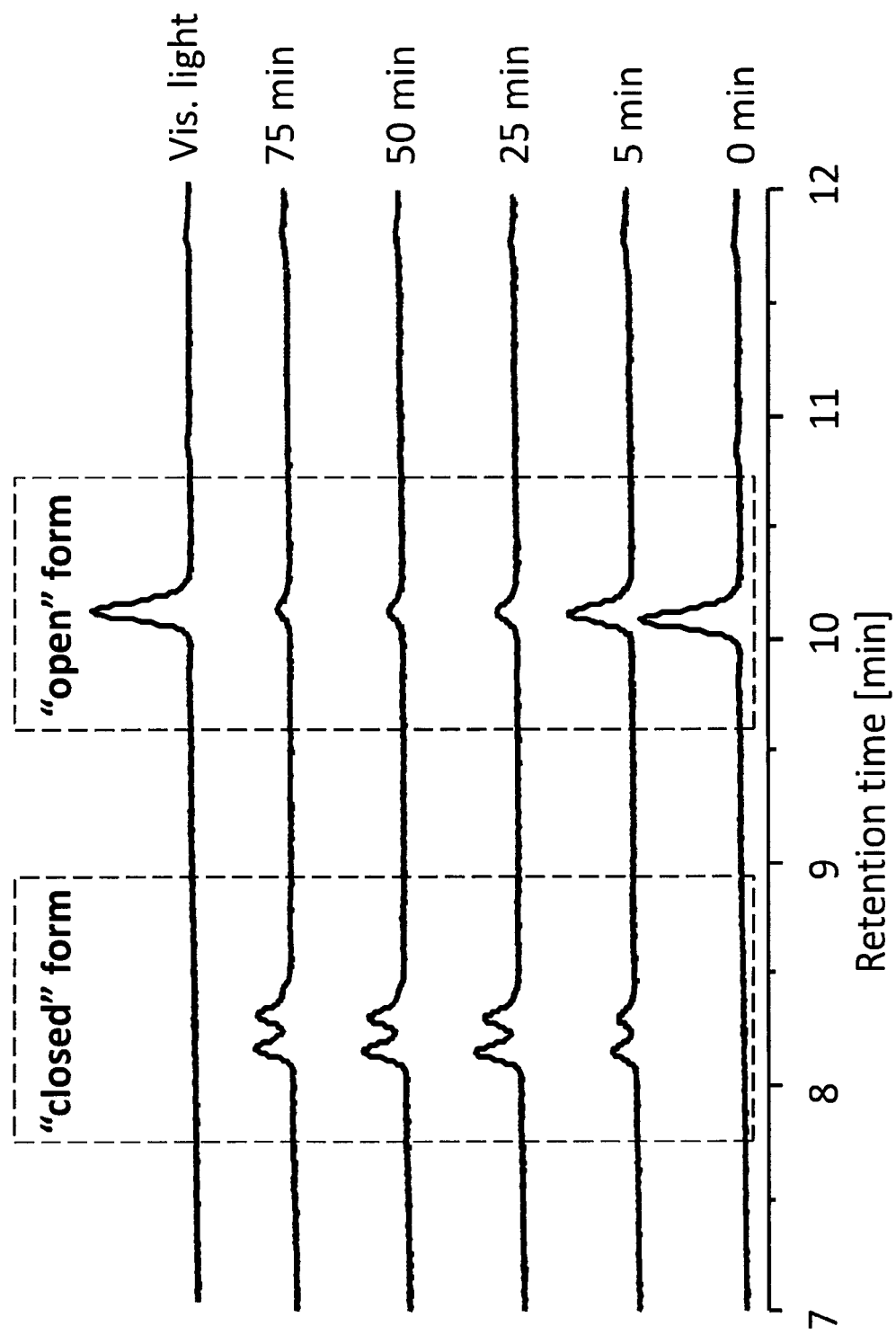
FIG. 3 shows analytical RP-HPLC chromatograms for GS-Sw(FP) acquired during the course of illumination of the peptidomimetic dissolved in a water-acetonitrile mixture, 3:1, 100 μg/ml by UV and visible light. The two neighboring peaks correspond to the two diastereomers of the "closed" form of the peptidomimetic (indicated).

The transformation proceed up to 35-80%, depending on the conditions (see FIGS. 2 and 3 for results on GS-Sw(FP)). The extent of conversion could be considerably enhanced by the addition of chaotropic agents to the solutions, when the GS analogues were switched to the "closed" in 1 M aq solution of urea (see below).

The reverse photo-conversion of the peptidomimetic GS-Sw(FP) from the "closed" to the "open" form by visible light was also tested. A solution of peptide in the pink-colored "closed"-form (in a water-acetonitrile mixture, 3:1, 100 µg/ml) was used. The conversion of the peptidomimetic from the "closed"-form to the "open"-form was determined by RP-HPLC (analytical C18 column, linear A:B gradient of 4% B/min, 1.5 ml/min flow rate) after 0.25, 1.5, 5.5, 7.5 min of irradiation by visible light. A bright halogen lamp (250 Watts) was used, and the solutions were placed in 10 cm distance from the light source. The obtained data fitted well to the exponential equation $y=1-\exp(t/T)$, where y is a conversion of "closed" form into the "open" form, t is the time of the illumination and r is the half-conversion time. In order to achieve 60% transformation, the time of illumination should be 7.5 min, while 80% conversion is achieved in 12.5 min, etc. The conversion from "closed" to "open" could be achieved to 100%.

Stock solutions were prepared for all seven HPLC-purified compounds (wild type GS, and both "open" and "closed" forms for each of the three peptidomimetics), with a concentration of 1 mg/ml as verified by analytical RP-HPLC. To prepare the stock solutions of GS and its analogues in "open" form, the corresponding compounds were weighed and dissolved in 50% ethanol to obtain the desired 1 mg/ml concentration. To prepare the stock solutions of the GS analogues in the "closed" form, the following procedure was used:

The compounds were dissolved at a concentration of 100 µg/ml in 1 M aq urea and exposed to UV light for 25 min as described above. The "open" and "closed" forms were separated using RP-HPLC (preparative C18 column, linear A:B gradient of 8% B/min, 17 ml/min flow rate) and lyophilized. The corresponding retention times are listed in Table 1. The lyophilized fractions corresponding to the "closed" form of the peptidomimetics were dissolved in a small amount of 50% ethanol, and the concentrations were determined by analytical RP-HPLC. All these manipulations were done in the dark.

TABLE 1

Retention times at which GS and its analogues were eluted from the analytical HPLC C18 column (Vydac ®, 4.6 × 250 mm) with a linear A:B gradient of 1% B/min and a 1.5 ml/min flow rate).

|  | GS | GS-Sw(LF), "open" | GS-Sw(FP), "open" | GS-Sw(PV), "open" | GS-Sw(LF), "closed" | GS-Sw(FP), "closed" | GS-Sw(PV), "closed" |
|---|---|---|---|---|---|---|---|
| RT[min] | 44.9 | 34.9 | 40.1 | 41.5 | 24.2 | 26.4 | 31.6 |

Figure 4:
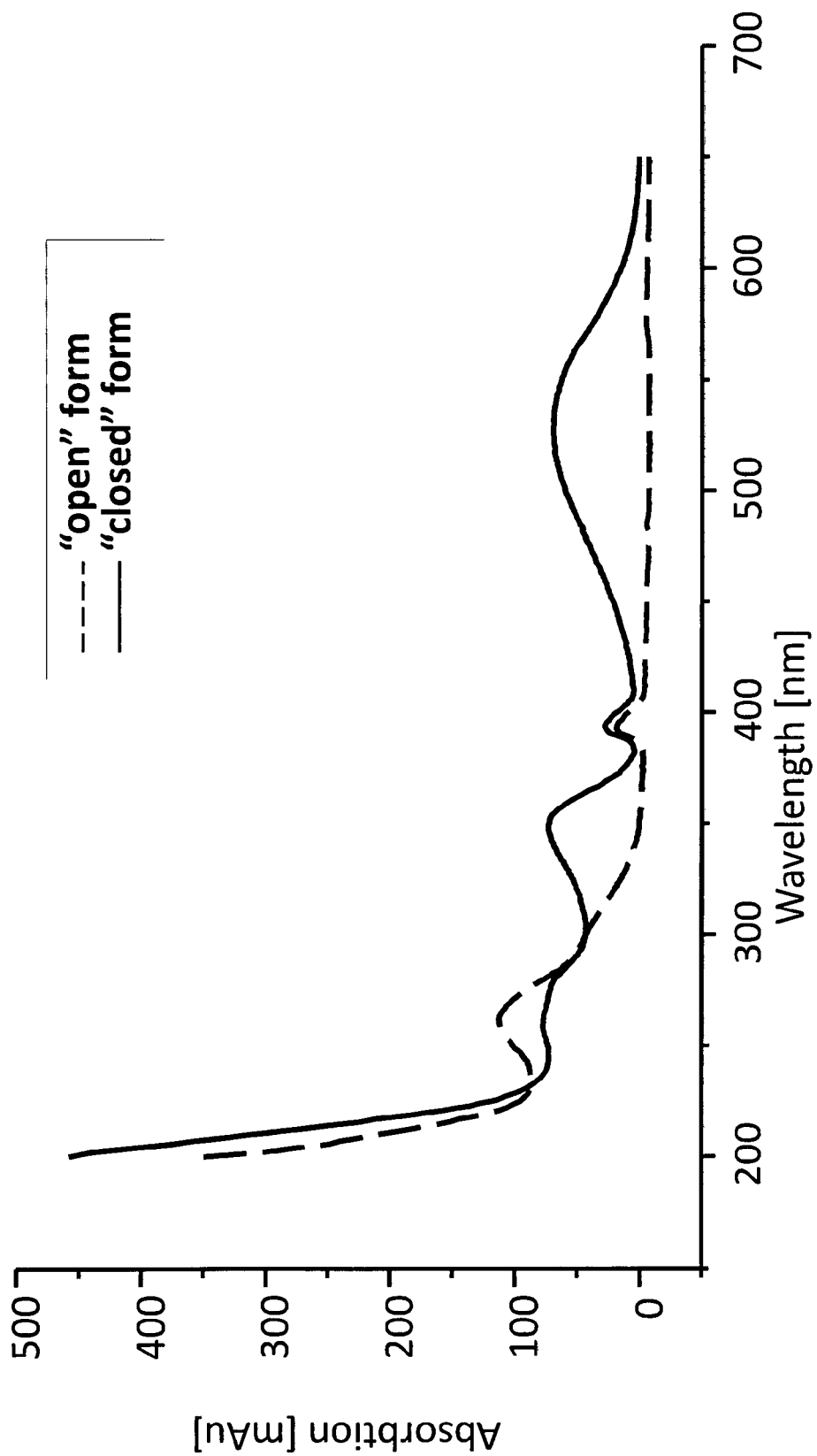
FIG. 4 shows UV/VIS absorbance spectra of the peptidomimetics, GS-Sw(FP) in the "open" (dotted line) and "closed" (solid line). The signal at 400 nm is an instrumental artifact.

The two isolated forms of the peptidomimetics have different absorbance spectra, showing the characteristics features of compounds bearing the diarylethene chromophores [M. Irie. Photochromism of diarylethene single molecules and single crystals. Photochem. Photobiol. Sci. 2010, 9, 1535-1542]. The UV/VIS absorbance spectra for one of the peptidomimetics, GS-Sw(FP) in the "closed" and "open" states are shown in FIG. 4.

EXAMPLE 4

Photo-Switching the Antimicrobial Activity

The antimicrobial activities of GS and its analogues were measured using broth microdilution assay using a standard protocol [Daniel Amsterdam (1996). Susceptibility testing of antimicrobials in liquid media. In: Antibiotics in laboratory medicine, Loman, V., ed., 4th ed. Williams and Wilkins, Baltimore, Md., pp. 52-111]. The peptidomimetic compounds were tested against bacteria strains *Escherichia coli* DSM 1103, *Staphylococcus aureus* DSM 1104, *Staphylococcus epidermidis* DSM 1708, and *Staphylococcus xylosus* DSM 20267. GS analogues in the "closed" form were prepared in advance by RP-HPLC and stored protecting them from light. The corresponding minimal inhibitory concentrations (MIC) are listed in Table 2, where a small MIC value indicates a high antimicrobial activity, and vice versa. All photo-switchable GS analogues are thus seen to have a good antimicrobial activity in the "open" form, while they are much less active when the photo-switch is in the rigid "closed" state.

many antimicrobial peptides when applied systemically, which hinders their application as drugs.

To test the hemolytic activities of GS and its analogues, conserved human blood samples were obtained from Karlsruhe municipal hospital and washed four times in Tris buffer, pH 7.6, at 4° C. Aliquots of the blood cells were incubated with different concentrations of the peptide/peptidomimetics for 30 min at 37° C. and subsequently centrifuged. The absorption of the supernatant at 540 nm gives the extent of hemolysis, relative to 0% as taken from the peptide-free control and 100% after treatment with Triton X-100 (not to interfere with this analysis, the samples with GS analogues in the "closed" form were back-converted to their "open" forms by 30 min exposure to the visible light). The $HC_{50}$ values, where 50% of the erythrocytes were lysed, were determined from the concentration dependent curves and are listed in Table 3. Small $HC_{50}$ values indicate a high hemolytic activity, and vice versa. All GS analogues in the "closed" state were much less hemolytic than in the "open" state, just as it was seen for their antimicrobial activities.

TABLE 2

Antimicrobial activities of GS and its photo-switchable analogues. Values of minimal inhibitory concentration (MIC) are given in µg/ml.

|  | GS | GS-Sw(LF), "open" | GS-Sw(FP), "open" | GS-Sw(PV), "open" | GS-Sw(LF), "closed" | GS-Sw(FP), "closed" | GS-Sw(PV), "closed" |
|---|---|---|---|---|---|---|---|
| *E. coli* | 8 | >128 | 128 | >128 | 64 | >128 | >128 |
| *S. aureus* | 2 | 8 | 4 | 4 | 128 | 32 | 16 |
| *S. epidermidis* | 2 | 16 | 8 | 4 | 128 | 64 | 32 |
| *S. xylosus* | 1 | 8 | 8 | 4 | 128 | 32 | 32 |

As seen in Table 2, it is possible to define therapeutically important concentration ranges in which the peptidomimetics in the "open" form suppress bacterial growth, while This proves by several independent assays that the biological activities of the photo-switchable GS analogues could be controlled by light.

TABLE 3

Values of 50% of hemolysis ($H_{50}$) for GS and its analogues in the "open" and "closed" forms each

|  | GS | GS-Sw(LF), "open" | GS-Sw(LF), "closed" | GS-Sw(FP), "open" | GS-Sw(FP), "closed" | GS-Sw(PV), "open" | GS-Sw(PV), "closed" |
|---|---|---|---|---|---|---|---|
| $H_{50}$, µg/ml | 12 | 47 | >>128 | 6.5 | 72 | 6 | 58 | being inactive in the "closed" form. One further experiment aimed at finding these optimal conditions for treatment with the peptidomimetic GS-SwFP is illustrated in FIG. 5.

EXAMPLE 5

Photo-Switching the Hemolytic Activity

Another biological activity of GS, GS-Sw(LF), GS-Sw (FP), and GS-Sw(PV), which is important for practical (in vivo) applications, is the hemolytic activity, and this can also be reversibly activated and deactivated by light. It should be noted that the hemolytic activity is the major side-effect of

EXAMPLE 6

Synthesis of the Photo-Switchable Building Block 4a

Synthesis of 6.

The 15 g of compound 5 (0.0456 mol) was dissolved in 250 ml of dried tetrahydrofuran under inert atmosphere of argon gas. The solution was cooled to −78° C. by cooling bath with dry ice. To the cooled solution were added 20 ml (0.051 mol) of the 2.5 M butyllithium solution in hexane. The reaction mixture was let go to the temperature −10° C. and then again was cooled to −78° C. 4 g (0.0548 mol) of the dimethylformamide was added to the solution at −78° C. The solution was slowly (during half an hour) heated to 0° C. and stirred at that temperature for one more hour. Then solution was poured into 200 ml of water and 55 ml (0.055 mol) of 1 M hydrochloric acid was added. The product 6 was extracted by 200 ml of diethyl ether. Separated organic phase was dried by anhydrous magnesium sulfate and volatile solvents were removed under reduced pressure. Obtained 15 g of crude material without purification was used in next synthetic step.

Synthesis of 7.

The 15 g of crude compound 6 (approximately 0.0456 mol) was dissolved in 250 ml of toluene; 7.1 g (0.0684 mol) of 2,2-dimethyl-1,3-propanediol and 0.1 g of p-toluenesulfonic acid were added. Then the solution was refluxed with Dean-Stark apparatus until all the water, which has been formed in the reaction process, was removed (0.82 g). Toluene was removed under reduced pressure. Pure product 7 was obtained after column chromatography on silica gel using n-hexane/ethyl acetate 10:1 as eluent. The yield was 14.2 g (76% of theoretical) in two steps from 5 to 7.

Synthesis of 9.

The 3 g (0.00733 mol) of compound 7 was dissolved in 50 ml of dried tetrahydrofuran under inert atmosphere of argon gas. The solution was cooled to −78° C. by cooling bath with dry ice. To the cooled solution were added 3.52 ml (0.0088 mol) of the 2.5 M butyllithium solution in hexane. The reaction mixture was let go to the temperature −10° C. and then again was cooled to −78° C. 2.27 g (0.0088 mol) of the compound 8 was added to the solution at −78° C. Compound 8 was synthesized analogously to the protocol published by Z. H. Zhou et al, *Heteroatom Chemistry*, 2003, 7, 603-606. DOI: 10.1002/hc.10195. The solution was slowly (during half an hour) heated to 0° C. and stirred at that temperature for one more hour. Then solution was poured into 100 ml of water and 9 ml (0.009 mol) of 1 M hydrochloric acid was added. The product 9 was extracted by 100 ml of diethyl ether. Separated organic phase was dried by anhydrous magnesium sulfate and volatile solvents were removed under reduced pressure. Pure product 9 was obtained after column chromatography on silica gel using as the eluent n-hexane/ethyl acetate 5:1. The yield was 3.1 g (73% of theoretical).

Synthesis of 10.

The 3.1 g (0.0064 mol) of compound 9 was dissolved in 40 ml of ethanol. Then 7.42 g (0.032 mol) of freshly prepared argentum oxide and 0.5 g (0.0128 mol) sodium hydroxide were added and actively stirred for two hours. 20 ml (0.02 mol) of 1 M hydrochloric acid and 40 ml of ethanol were added. Formed precipitate was filtered on a paper filter and the solution with the product 10 was extracted twice by 100 ml of diethyl ether. Separated organic phases were combined and dried by anhydrous magnesium sulfate and volatile solvents were removed under reduced pressure. The yield was 3.2 g (100% of theoretical) of pure compound 10.

Synthesis of 4a.

The 3.2 g (0.0064 mol) of compound 10 was dissolved in 20 ml of dichloromethane. 2 ml of trifluoroacetic acid was added to the solution and solution was incubated for 2 hours at room temperature. Then volatile solvents were removed under reduced pressure. Then obtained yellow oil was dissolved in 50 ml of water/acetone 1:1. 1,075 g (0.0128 mol) of sodium bicarbonate and 3.3 g (0.0128 mol) of fluorenylmethoxycarbonyl chloride were added. Solution was kept under stirring for 4 hours at room temperature. Then slowly 12.8 ml (0.0128 mol) of 1 M hydrochloric were added and product 4a was extracted twice by 100 ml of diethyl ether. Separated organic phases were combined and dried by anhydrous magnesium sulfate and volatile solvents were removed under reduced pressure. Pure compound 4a was obtained after column chromatography on silica gel with eluent n-hexane/ethyl acetate 5:1. The yield was 4 g (91% of theoretical).

Scheme 3: Synthesis of compound 4a

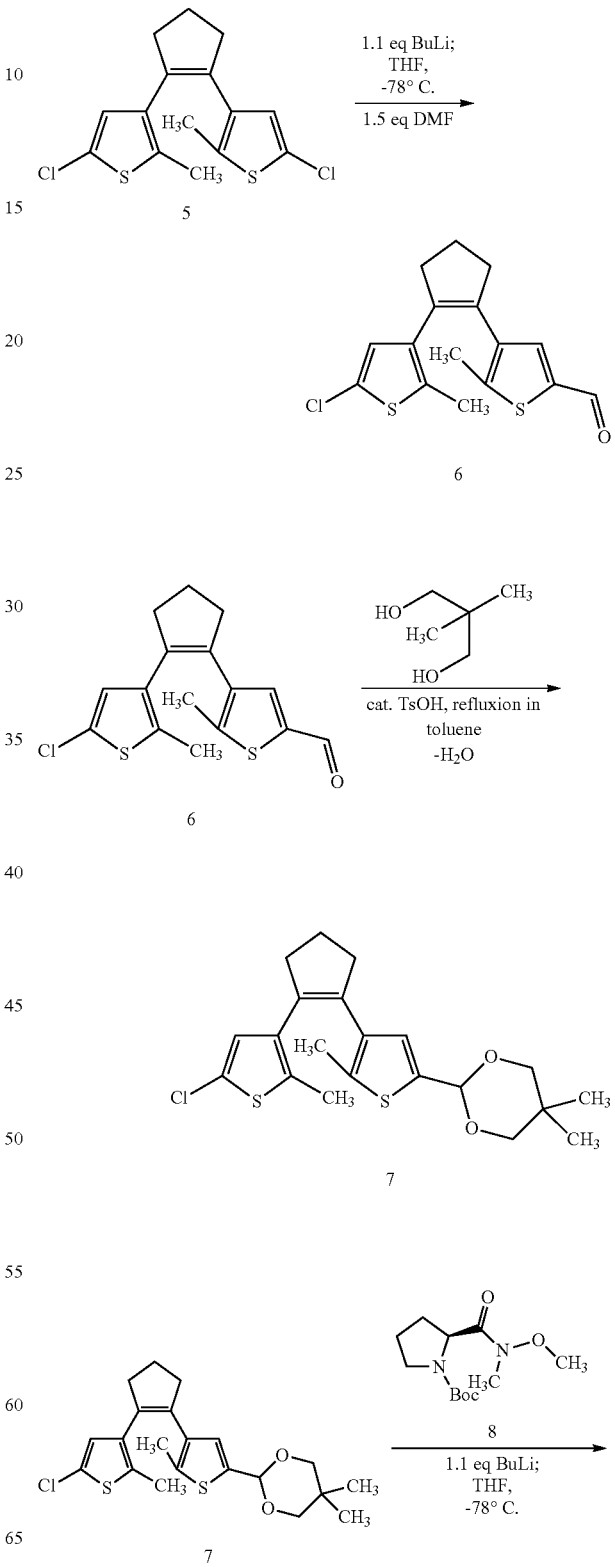

EXAMPLE 7
Synthesis of Compound 4b
Compound 4b was synthesized using the same protocols as in the case of 4a preparation.
Scheme 4: Synthesis of compound 4b
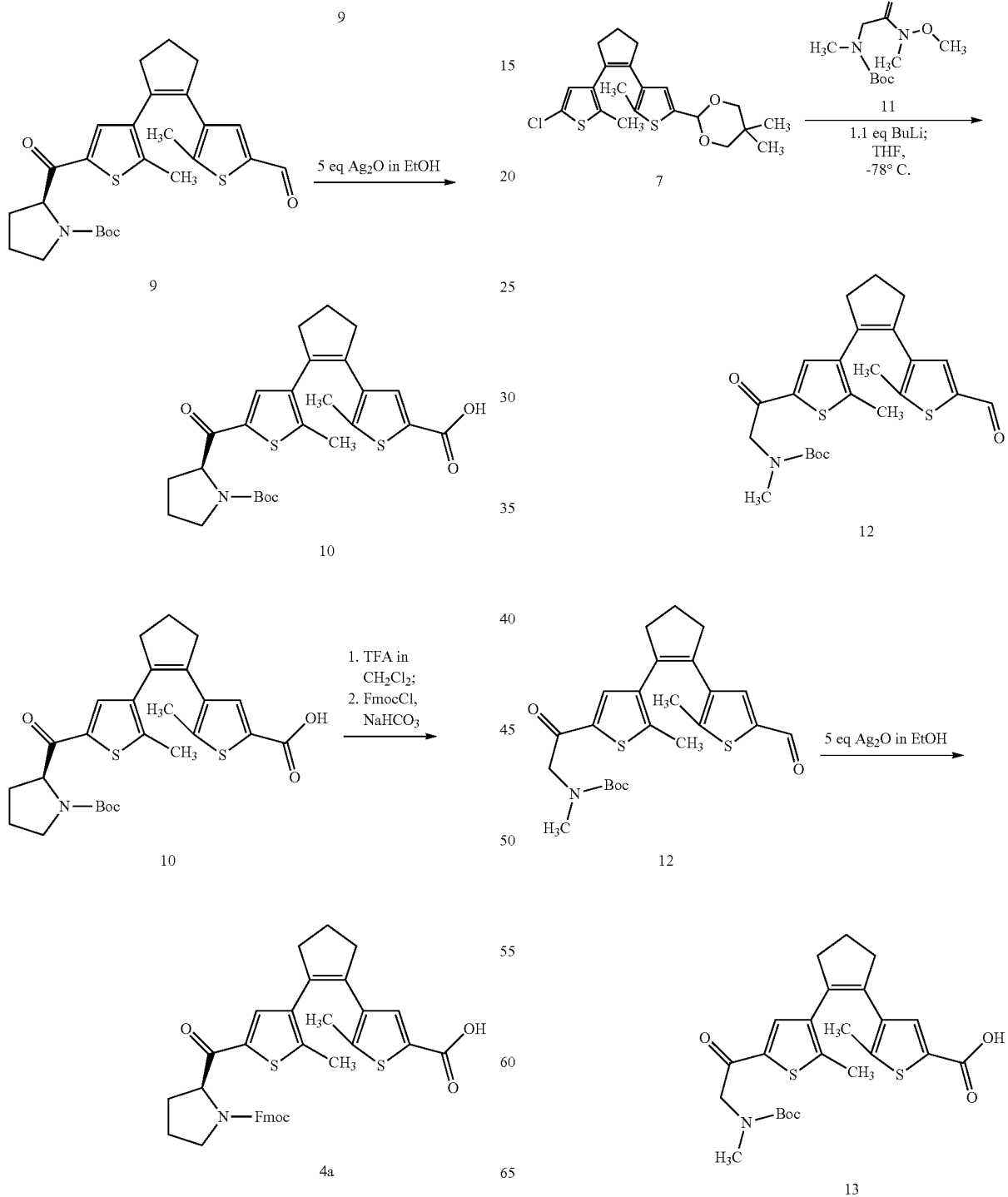

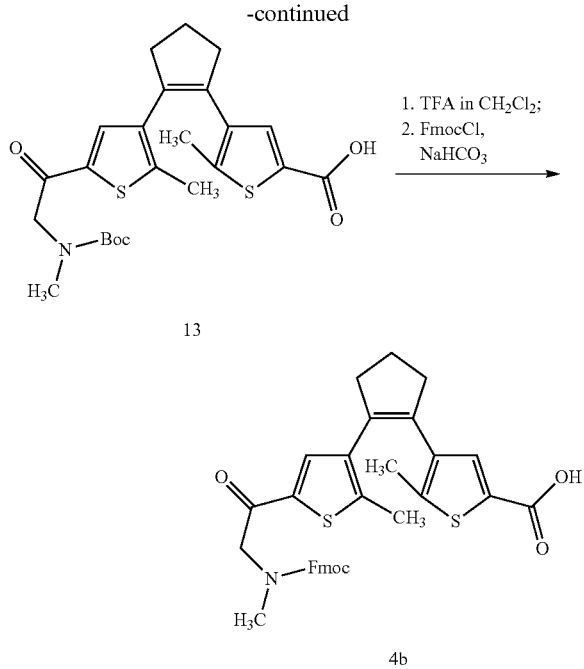

EXAMPLE 8

Synthesis of Compound 4c

Synthesis of 14.

The 3 g of compound 7 (0.0073 mol) was dissolved in 75 ml of dried tetrahydrofuran under inert atmosphere of argon. The solution was cooled to −78° C. by cooling bath with dry ice. To the cooled solution were added 3.52 ml (0.0088) of the 2.5 M butyllithium solution in hexane. The reaction mixture was let go to the temperature −10° C. and then again was cooled to −78° C. 1.08 g (0.0088 mol) of the ethyl chloroacetate was added to the solution at −78° C. The solution as slowly (during half an hour) heated to 0° C. and stirred at that temperature for one more hour. Then solution was poured into 200 ml of water and 55 ml (0.055 mol) of 1M hydrochloric acid was added. The product 6 was extracted by 200 ml of diethyl ether. Separated organic phase was dried by anhydrous magnesium sulfate and volatile solvents were removed under reduced pressure. Pure compound 14 was obtained after column chromatography on silica gel with eluent n-hexane/ethyl acetate 4:1. The yield was 1.8 g (54% of theoretical).

Synthesis of 15.

Converting compound 14 to 15 was done using the same protocol as for converting compound 9 to 10 with 100% yield.

Synthesis of 16.

1.8 g (0.00472 mol) of compound 15 was dissolved in 20 ml water/ethanol 1:1. 0.5 g (0.0076 mol) of sodium azide was added. The reaction mixture was stirred for 24 hours at 40° C. Then 50 ml of water were added and the product 16 was extracted by 100 ml of diethyl ether. Organic phase was dried by anhydrous magnesium sulfate and volatile solvents were removed under reduced pressure. Obtained 1.81 g of crude material was used in the next synthetic step without purification.

Synthesis of 4c.

1.81 g (0.00470 mol) of compound 16 was dissolved in 20 ml of methanol in a 500 ml volume glass. 100 mg of palladium, 10% on carbon, were added. The air from the glass was pumped off and hydrogen gas was pumped in. Afterwards the glass was connected to the balloon with hydrogen gas and solution was kept under stirring for 4 hours at room temperature. Then glass was connected to vacuum in order to remove the hydrogen gas and the solution was filtered. Methanol was removed yielding yellow oil. Then obtained yellow oil was dissolved in 50 ml of water/acetone 1:1. 0.79 g (0.0094 mol) of sodium bicarbonate and 2.4 g (0.0094 mol) of fluorenylmethoxycarbonyl chloride were added. Solution was actively stirred for 4 hours at room temperature. Then slowly 9.4 ml (0.0094) of 1 M hydrochloric acid were added and product 4a was extracted twice by 100 ml of diethyl ether. Separated organic phases were combined and dried by anhydrous magnesium sulfate and volatile solvents were removed under reduced pressure. Pure compound 4b was obtained after column chromatography on silica gel with eluent n-hexane/ethyl acetate 5:1. The yield was 2.74 g (90% of theoretical).

Scheme 5: Synthesis of compound 4c

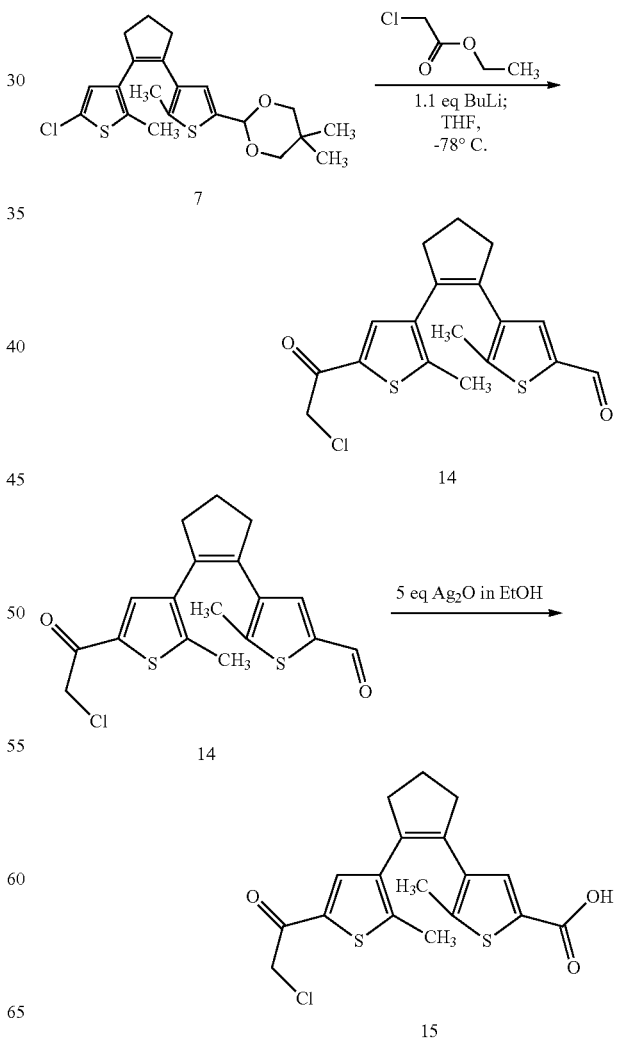

29
-continued

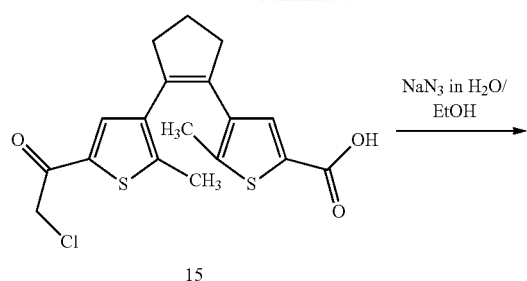
15

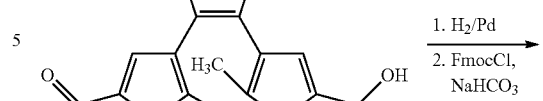

30
-continued

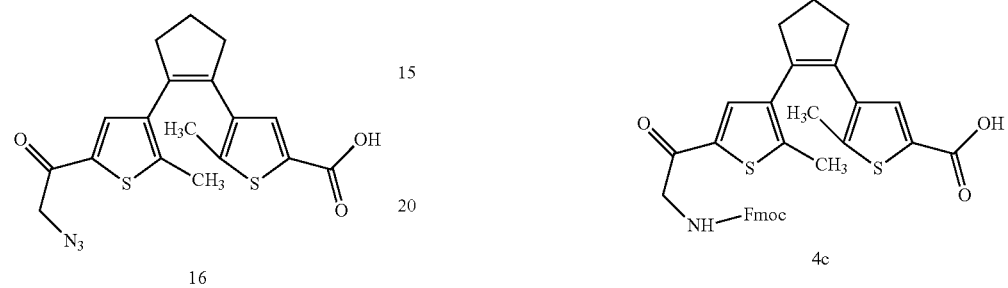

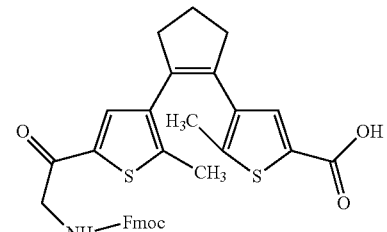
4c

The invention claimed is:

1. A peptidomimetic compound represented by the general formula Ia or a salt thereof,

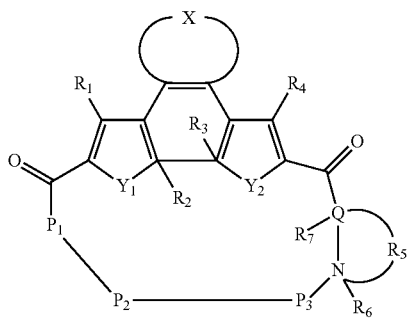

wherein
- $R_1$ and $R_4$ are independently selected from the group consisting of H, an alkyl group, alkenyl group, alkynyl group, alkoxy group, aryl group, heteroaryl group, cyano group, nitro group, phosphate group and sulfoxyl group;
- $R_2$ and $R_3$ are independently selected from the group consisting of an alkyl group, alkenyl group, alkynyl group, alkoxy group, aryl group, heteroaryl group, cyano group, nitro group, phosphate group and sulfoxyl group;
- X represents $-(CH_xF_y)_z-$, wherein x+y=2, x=0, 1 or 2, y=0, 1 or 2 and z=2 to 4;
- $Y_1$ are independently selected from S, $SO_2$, N, N-alkyl, or O;
- $P_1$ and $P_3$ each independently represents a single amino acid residue or a peptide sequence of 2 or more amino acid residues;
- $P_2$ is absent or represents a single amino acid residue or a peptide sequence of 2 or more amino acid residues;
- Q is C or N;
- $R_5$ is selected from H, an alkyl group, heteroalkyl group, alkenyl group, heteroalkenyl group, alkynyl group or a heteroalkynyl group, and is bound to Q or may form a ring together with Q and N, or $R_5$ is absent;
- $R_6$ is selected from H, an alkyl group, heteroalkyl group, alkenyl group, heteroalkenyl group, alkynyl group, heteroalkynyl group, alkoxy group, aryl group, and heteroaryl group, or is absent; and
- $R_7$ is selected from H, a natural amino acid side chain, an alkyl group, heteroalkyl group, alkenyl group, heteroalkenyl group, alkynyl group, heteroalkynyl group, alkoxy group, aryl group or a heteroaryl group; with the proviso that when $P_2$ is absent, $P_1$ and $P_3$ are not bonded to each other;
with the proviso that when Q is N, $R_5$ is absent, and
with the proviso that when $R_5$ forms a ring together with Q and N, $R_6$ is absent.

2. A peptidomimetic compound represented by the general formula Ib or a salt thereof,

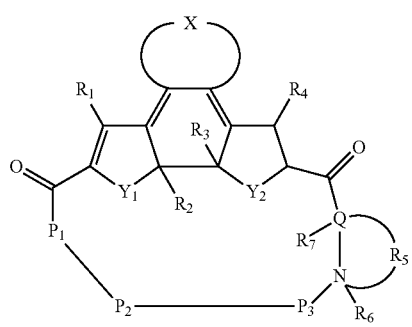

wherein $R_1$ to $R_4$, X, $Y_1$, $Y_2$, $P_1$ to $P_3$, Q, and $R_5$ to $R_7$ are as defined in claim 1, with the proviso that when $P_2$ is absent, $P_1$ and $P_3$ are not bonded to each other; with the proviso that when Q is N, $R_5$ is absent, and
with the proviso that when $R_5$ forms a ring together with Q and N, $R_6$ is absent.

3. The peptidomimetic compound according to claim 1, wherein $R_1$ and $R_4$ are independently selected from H and a $C_1$-$C_6$ alkyl group, $R_2$ and $R_3$ are independently selected from a methyl group and an ethyl group and X is $-CH_2CH_2CH_2-$ or $-CF_2CF_2CF_2-$.

4. The peptidomimetic compound according to claim 1, wherein each of $R_1$ and $R_4$ is H, each of $R_2$ and $R_3$ is a methyl group, X is $-CH_2CH_2CH_2-$ or $-CF_2CF_2CF_2-$, and each of $Y_1$ and $Y_2$ is S.

5. The peptidomimetic compound according to claim 1, represented by the following formulae GS-Sw (LF), GS-Sw (FP) and GS-Sw (PV):

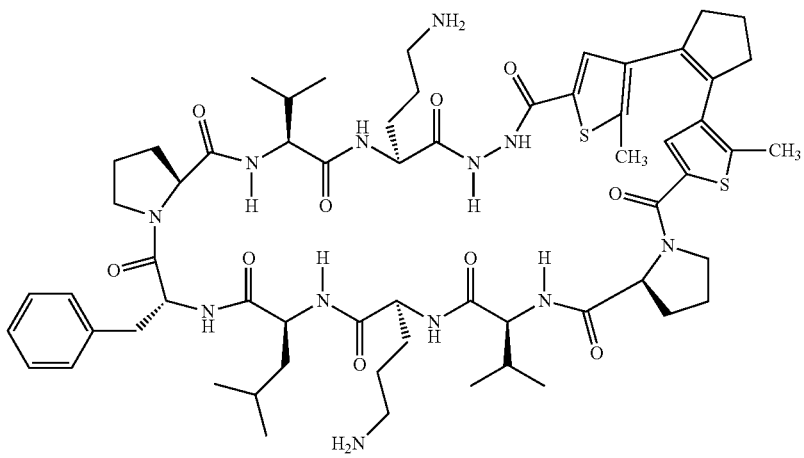

GS-Sw(LF)

-continued
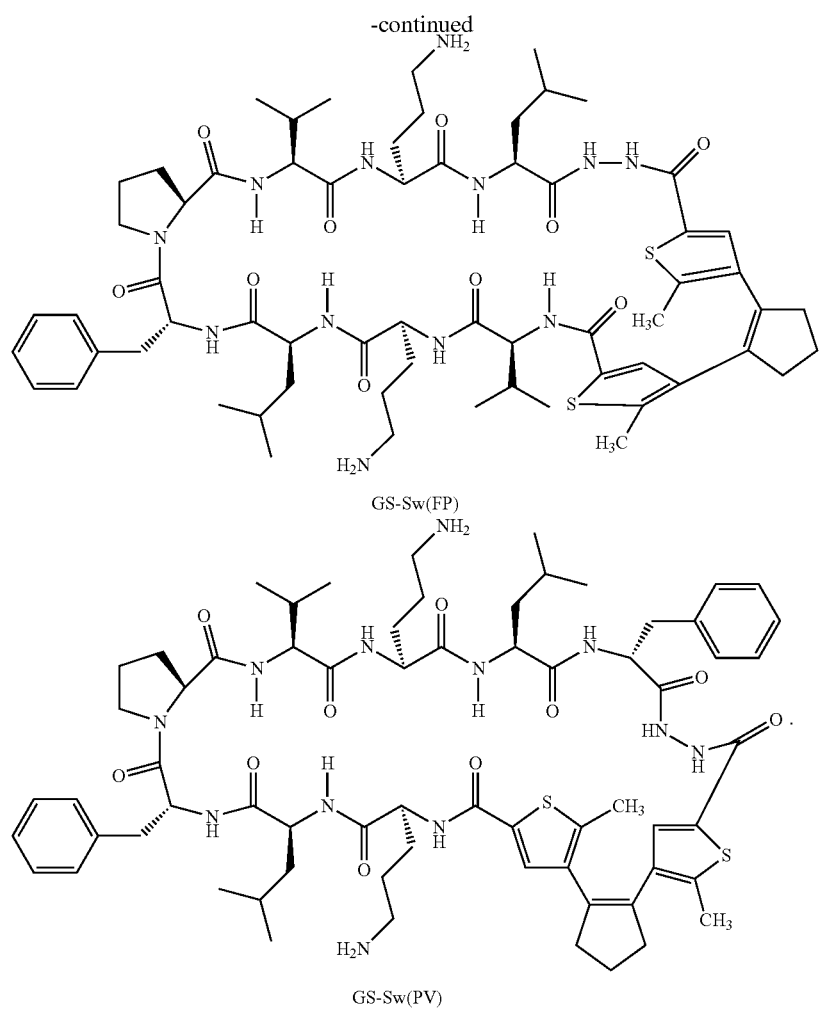
GS-Sw(FP)
GS-Sw(PV)
* * * * *